United States Patent
Sakairi

(10) Patent No.: US 10,948,479 B2
(45) Date of Patent: Mar. 16, 2021

(54) METHOD FOR DISEASE DIAGNOSIS BASED ON METABOLITE IN URINE

(71) Applicant: HITACHI, LTD., Tokyo (JP)

(72) Inventor: Minoru Sakairi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 201 days.

(21) Appl. No.: 16/081,566

(22) PCT Filed: Jun. 9, 2017

(86) PCT No.: PCT/JP2017/021421
§ 371 (c)(1),
(2) Date: Aug. 31, 2018

(87) PCT Pub. No.: WO2017/213246
PCT Pub. Date: Dec. 14, 2017

(65) Prior Publication Data
US 2019/0094205 A1    Mar. 28, 2019

Related U.S. Application Data

(60) Provisional application No. 62/348,252, filed on Jun. 10, 2016, provisional application No. 62/433,450, filed on Dec. 13, 2016.

(51) Int. Cl.
| | |
|---|---|
| *G01N 33/493* | (2006.01) |
| *G01N 33/574* | (2006.01) |
| *G16H 10/40* | (2018.01) |
| *G01N 27/62* | (2021.01) |
| *G16H 50/30* | (2018.01) |
| *G01N 33/68* | (2006.01) |

(52) U.S. Cl.
CPC .......... *G01N 33/493* (2013.01); *G01N 27/62* (2013.01); *G01N 33/57415* (2013.01); *G01N 33/57419* (2013.01); *G01N 33/6848* (2013.01); *G16H 10/40* (2018.01); *G16H 50/30* (2018.01)

(58) Field of Classification Search
None
See application file for complete search history.

(56) References Cited

U.S. PATENT DOCUMENTS

2010/0017145 A1    1/2010 Imaizumi et al.
2017/0016906 A1    1/2017 Hirotsu et al.

FOREIGN PATENT DOCUMENTS

| CN | 102323351 A | 1/2012 |
| EP | 3 156 499 A | 4/2017 |

OTHER PUBLICATIONS

Huang, J. et al. Analysis of multiplex endogenous estrogen metabolites in human urine using ultra-fast liquid chromatography—tandem mass spectrometry: A case study for breast cancer, Analytica Chimica Acta 711 (2012) 60-68 (Year: 2012).*

(Continued)

*Primary Examiner* — Xiaoyun R Xu
(74) *Attorney, Agent, or Firm* — Baker Botts L.L.P.

(57) ABSTRACT

The present invention relates to a method, a device, and a kit for detecting a cancer, predicting a cancer risk, determining a cancer stage, determining a cancer prognosis, and/or evaluating the effectiveness of a treatment in a subject by measuring a urinary metabolite in the subject, and a method for testing a cancer.

7 Claims, 41 Drawing Sheets

(56) References Cited

OTHER PUBLICATIONS

Estrone Mass Spectrum, MassBank Record:FFF00241, 2011, retrieved from internet: https://massbank.eu/MassBank/Record Display.jsp?id=FFF00241 (Year: 2011).*

"Study on metabolic spectrum characteristics of blood and urine from colorectal cancer using combined chromatography-mass," Chinese Master's Theses Full-text Database Medicine and Health Sciences, No. 9 E072-109, Sep. 15, 2015 (partial English translation attached).

Office Action, dated Apr. 15, 2020, which issued during the prosecution of Chinese Application No. 201780010593.1, which corresponds to the present application (English translation attached).

International Search Report, dated Aug. 22, 2017, which issued during the prosecution of International Application No. PCT/JP2017/021421, which corresponds to the present application.

Office Action, dated Sep. 22, 2020, which issued during the prosecution of Chinese Application No. 201780010593.1, which corresponds to the present application (English translation attached).

* cited by examiner

Fig. 5A

BREAST CANCER/COLON CANCER/HEALTHY INDIVIDUAL

| RANDOM FOREST | | PREDICTION GROUP | | | ERROR |
|---|---|---|---|---|---|
| | | BREAST CANCER | COLON CANCER | HEALTHY | |
| ACTUAL GROUP | BREAST CANCER | 14 | 1 | 0 | 0.0667 |
| | COLON CANCER | 1 | 14 | 0 | 0.0677 |
| | HEALTHY | 0 | 0 | 15 | 0.0000 |

PREDICTION ACCURACY: 95.56%

BREAST CANCER/HEALTHY INDIVIDUAL

| RANDOM FOREST | | PREDICTION GROUP | | ERROR |
|---|---|---|---|---|
| | | BREAST CANCER | HEALTHY | |
| ACTUAL GROUP | BREAST CANCER | 15 | 0 | 0.0000 |
| | HEALTHY | 0 | 15 | 0.0000 |

PREDICTION ACCURACY: 100%

COLON CANCER/HEALTHY INDIVIDUAL

| RANDOM FOREST | | PREDICTION GROUP | | ERROR |
|---|---|---|---|---|
| | | BREAST CANCER | HEALTHY | |
| ACTUAL GROUP | COLON CANCER | 15 | 0 | 0.0000 |
| | HEALTHY | 0 | 15 | 0.0000 |

PREDICTION ACCURACY: 100%

Fig. 6A

BREAST CANCER/COLON CANCER/HEALTHY INDIVIDUAL

| RANDOM FOREST | | PREDICTION GROUP | | | ERROR |
|---|---|---|---|---|---|
| | | BREAST CANCER | COLON CANCER | HEALTHY | |
| | PREDICTION ACCURACY: 93.33% | | | | |
| ACTUAL GROUP | BREAST CANCER | 13 | 1 | 1 | 0.1333 |
| | COLON CANCER | 1 | 14 | 0 | 0.0677 |
| | HEALTHY | 0 | 0 | 15 | 0.0000 |

BREAST CANCER/HEALTHY INDIVIDUAL

| RANDOM FOREST | | PREDICTION GROUP | | ERROR |
|---|---|---|---|---|
| | | BREAST CANCER | HEALTHY | |
| | PREDICTION ACCURACY: 93.33% | | | |
| ACTUAL GROUP | BREAST CANCER | 13 | 2 | 0.1333 |
| | HEALTHY | 0 | 15 | 0.0000 |

COLON CANCER/HEALTHY INDIVIDUAL

| RANDOM FOREST | | PREDICTION GROUP | | ERROR |
|---|---|---|---|---|
| | | BREAST CANCER | HEALTHY | |
| | PREDICTION ACCURACY: 96.67% | | | |
| ACTUAL GROUP | COLON CANCER | 14 | 1 | 0.0667 |
| | HEALTHY | 0 | 15 | 0.0000 |

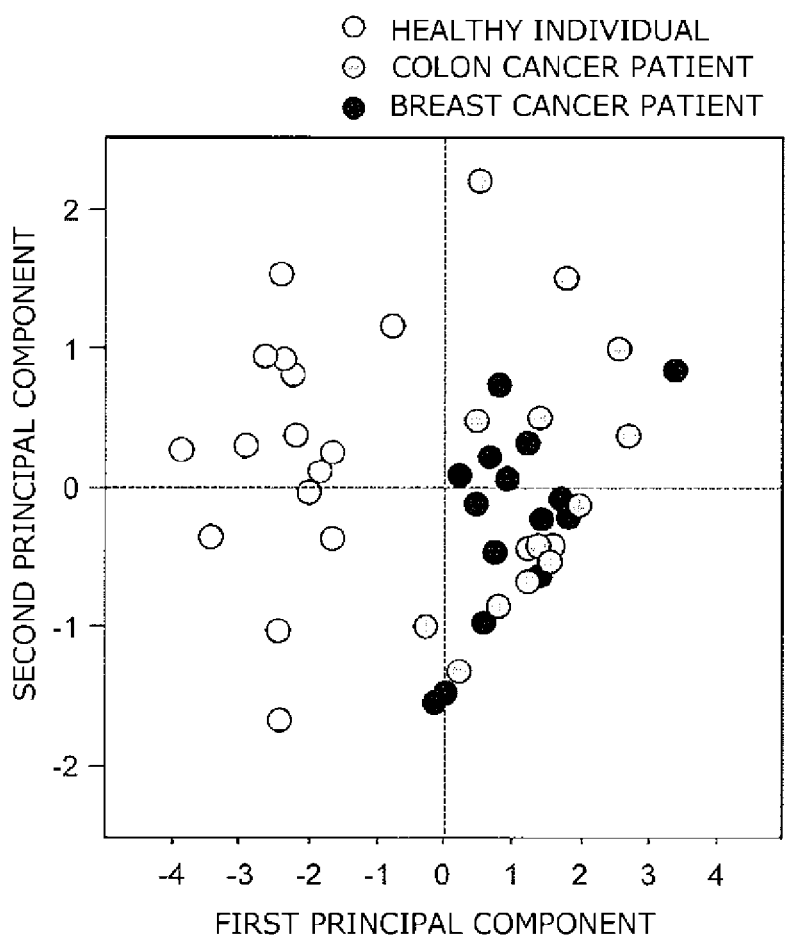

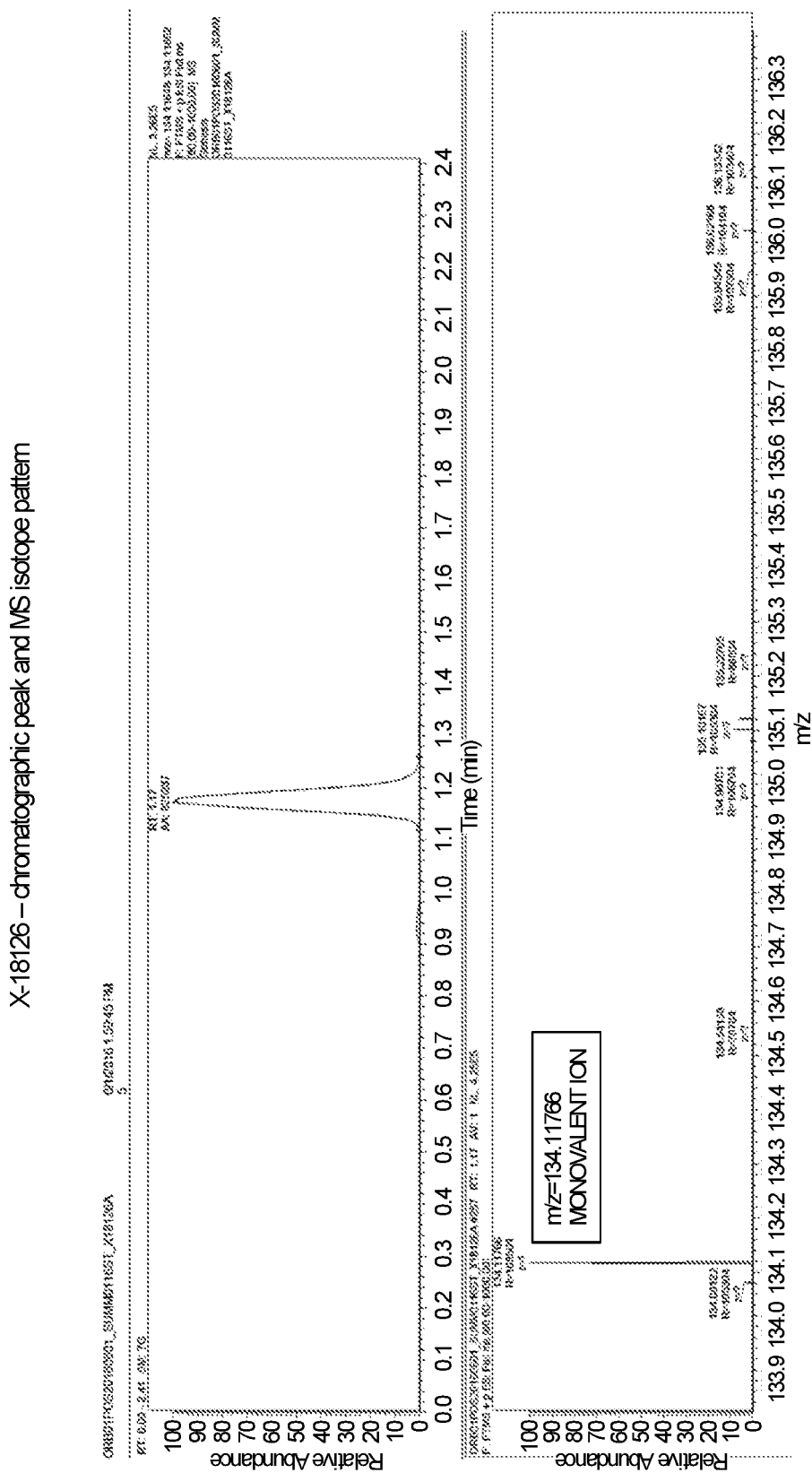

X-24502 – chromatographic peak and MS isotope pattern

METHOD FOR DISEASE DIAGNOSIS BASED ON METABOLITE IN URINE

This application is a U.S. National Phase application under 35 U.S.C. § 371 of International Application No. PCT/JP2017/021421, filed on Jun. 9, 2017, which claims priority based on U.S. Provisional Application No. 62/348,252 filed on Jun. 10, 2016 and U.S. Provisional Application No. 62/433,450 filed on Dec. 13, 2016. The International Application was published in Japanese on Dec. 14, 2017 as WO 2017/213246 A1 under PCT Article 21(2). The contents described in the specification and/or drawings of these patent applications are incorporated herein by reference.

TECHNICAL FIELD

The present invention relates to a method, a kit, and a device for analyzing a disease, particularly a cancer state of a subject based on the information of a metabolite in the urine of the subject.

BACKGROUND ART

Due to the medical costs in Japan exceeding 40 trillion yen and further acceleration of the declining birthrate and aging population, a shortage of social security costs in future has become a big social problem. For example, the costs for cancer disease in Japan amount to about 10 trillion yen when including direct and indirect costs (surveyed by Department of Public Health Policy, National Institute of Public Health). In order to largely reduce the costs for cancer disease, only the enhancement of the accuracy of diagnostic techniques based on the current consultation in hospitals does not suffice, and a stage, at which a social system associated with the diagnosis or treatment of a cancer itself should be largely changed by correction of medical disparities among populated areas and underpopulated areas by consultation through mail, a drastic reduction in disease costs by early detection of breast cancer or the like, the expansion of large-scale screening test for all cancer types or each cancer type, development of a test kit, or the like, has been reached.

For this purpose, AminoIndex Technology in which a cancer risk is determined by measuring an amino acid level in blood has been developed (PTL 1), and a study of a method for diagnosing a cancer using microRNA in blood has been performed mainly in National Cancer Center (PTL 2). However, these are tests using blood, and therefore, the situation is still the same that it is necessary to collect blood in hospitals.

On the other hand, Kyushu University has reported a cancer test using the olfaction system of *C. elegans*, which has attracted great attention due to its simplicity (PTL 3). However, unlike the conventional in vitro diagnostic methods, the test uses "live *C. elegans*", and therefore, it is necessary to introduce a new method for a large-scale test, quality control, and automatic analysis. In addition, in order that the above examination is approved as a diagnostic method in the future, it is also very important to elucidate the cancer detection mechanism in *C. elegans*.

CITATION LIST

Patent Literature

PTL 1: US Patent Application Publication No. 2010/017145 A

PTL 2: European Patent Application Publication No. 3156499 A

PTL 3: US Patent Application Publication No. 2017016906 A

SUMMARY OF INVENTION

Technical Problem

An object of the present invention is to specify a metabolite which increases or decreases between healthy individuals and cancer patients by performing a comprehensive analysis of metabolites in the urine of healthy individuals and cancer patients, and to examine a possibility of a cancer test using urine from the viewpoint of a metabolite analysis based on a multivariate analysis.

That is, the present invention relates to a method, a device, and a kit for detecting a cancer, predicting a cancer risk, determining a cancer stage, determining a cancer prognosis, and/or evaluating the effectiveness of a treatment in a subject by measuring a urinary metabolite in the subject.

Specifically, in one aspect, it is provided a method for evaluating a cancer, comprising:
measuring a urinary metabolite in a urine sample derived from a subject; and
evaluating a cancer in the subject based on the measurement results.

In another aspect, it is provided a method for evaluating the effectiveness of a treatment on a cancer, comprising:
measuring a urinary metabolite in a urine sample from an animal having a cancer and having received a treatment with a test therapeutic agent or a test therapeutic method; and
evaluating the effectiveness of the test therapeutic agent or the test therapeutic method on a cancer based on the measurement results.

Further, in other aspect, it is provided a kit for evaluating a cancer, comprising a means for measuring a urinary metabolite in a urine sample.

In still other aspect, it is provided a device for evaluating a cancer, comprising:
a measurement section which is configured to measure a urinary metabolite in a urine sample;
a comparison section which is configured to compare the measured value of the urinary metabolite measured by the measurement section with a reference or a previously measured value; and
a determination section which is configured to evaluate a cancer based on the comparison results obtained by the comparison section.

In other aspect, it is provided a method for testing a cancer, comprising:
receiving an input of the selection of a urinary metabolite to be used in a test as a primary test or the number of urinary metabolites;
performing a multivariate analysis of the measured value in a urine sample derived from a test subject with respect to the input urinary metabolite or the input number of urinary metabolites;
storing test results of the multivariate analysis; and
outputting the test results as primary test results,
wherein in the selection of the urinary metabolite or the number thereof, the selection is performed from 2 types, 3 types, 4 to 8 types, 9 to 19 types, or 20 to 30 types of urinary metabolites.

Advantageous Effects of Invention

According to the present invention, a method, a device, and a kit for evaluating a cancer with low invasiveness and simply at low cost are provided. Therefore, the present invention may be useful in the fields of cancer diagnosis, cancer testing, therapeutic evaluation, drug discovery, and the like.

BRIEF DESCRIPTION OF DRAWINGS

FIG. 5A is a table showing prediction accuracy using urinary marker candidates (including metabolites with an unknown structure and metabolites with a known structure) by a Random Forest analysis. It is found that the prediction accuracy is high and the urinary markers are effective.

FIG. 6A is a table showing prediction accuracy using urinary marker candidates (metabolites with a known structure) by a Random Forest analysis. It is found that the prediction accuracy is high and the urinary markers are effective.

FIG. 9B is a graph showing the effectiveness of urinary markers (3 types) by a principal component analysis which is one type of multivariate analysis.

FIG. 10 shows LC/MS data for the metabolite X-18126.

FIG. 16-1 shows MS/MS data for the metabolite X-16567.

FIG. 16-2 shows LC/MS data for the metabolite X-16567 (in the positive ion detection mode and the negative ion detection mode).

FIG. 18-1 shows MS/MS data for the metabolite X-11440.

FIG. 18-2 shows MS/MS data for the metabolite X-11440.

FIG. 20-1 shows MS/MS data for the metabolite X-12831.

FIG. 20-2 shows LC/MS data for the metabolite X-12831 (in the positive ion detection mode and the negative ion detection mode).

FIG. 22-1 shows MS/MS data for the metabolite X-12636.

FIG. 22-2 shows LC/MS data for the metabolite X-12636 (in the positive ion detection mode and the negative ion detection mode).

FIG. 24-1 shows MS/MS data for the metabolite X-24502.

FIG. 24-2 shows LC/MS data for the metabolite X-24502 (in the positive ion detection mode and the negative ion detection mode).

FIG. 26-1 shows MS/MS data for the metabolite X-23787.

FIG. 26-2 shows LC/MS data for the metabolite X-23787 (in the positive ion detection mode and the negative ion detection mode).

DESCRIPTION OF EMBODIMENTS

Figure 1:
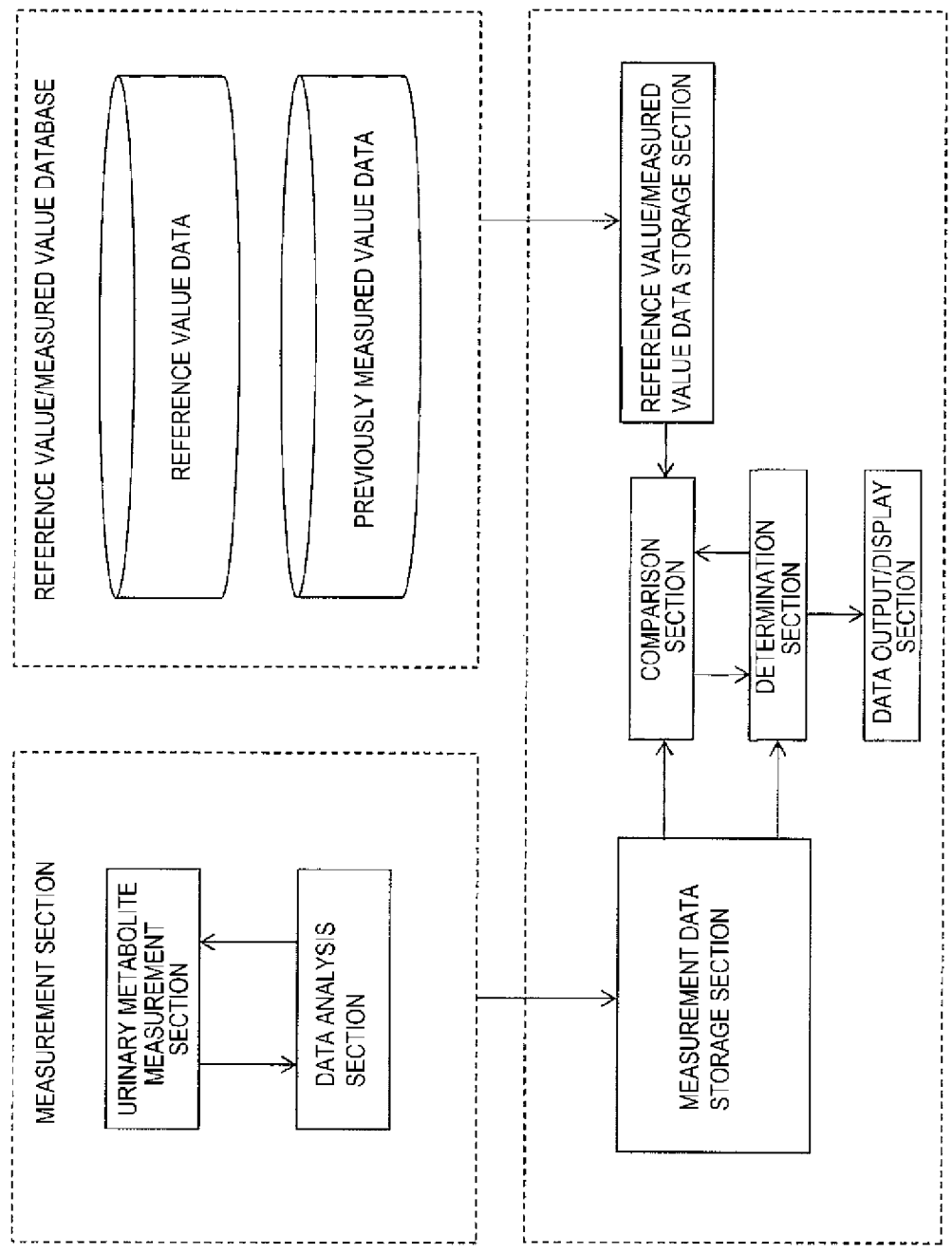
FIG. 1 is a view showing one embodiment of a device for evaluating a cancer.

According to a method, a device, and a kit provided by the present invention, a new urinary marker and a marker group associated with a cancer, particularly breast cancer and colon cancer are used. The urinary markers are metabolites whose level in urine varies depending on the onset or progression of a cancer, and therefore may be useful for detecting a cancer, predicting a cancer risk, determining a cancer stage, determining a cancer prognosis, and/or evaluating the effectiveness of a treatment, etc.

Therefore, the method for evaluating a cancer according to the present invention includes measuring a urinary metabolite in a urine sample derived from a subject, and evaluating a cancer in the subject based on the measurement results.

The term "urinary metabolite" or "urinary marker" or "biomarker" means a urinary metabolite to be measured for detection of a cancer or the like, that is, any of urinary metabolites listed in the following table. Further, the "marker group" is a combination composed of two or more urinary markers. The "measuring" means determining the relative abundance or absolute concentration of a metabolite in a urine sample. The relative abundance is the ratio of the measured intensity of a target metabolite with respect to a standard substance added intentionally. On the other hand, the absolute concentration is obtained by a method in which with respect to a target metabolite, a calibration curve (a relationship between the concentration of the metabolite and the measured intensity of the metabolite) is created in advance using the same metabolite, and the absolute concentration is calculated from the measured intensity. Further, in the present invention, the "measuring a urinary marker" may be measuring a metabolite which is a urinary marker or may be measuring a secondary substance or a derivative thereof. The "secondary substance" and the "derivative" mean a substance secondarily generated from a metabolite which is a urinary marker and a substance derived from the metabolite, respectively. The "secondary substance" and the "derivative" include, for example, a fragment of a metabolite, a modified metabolite, etc., but these are not limited thereto.

Main urinary markers to be used in the present invention are summarized in the following Table 1. In the table, in the column "Mass", a mass detected by a detection means described in the column "Detection platform" is shown. In the column "Detection platform", "LC/MS neg" and "LC/MS pos early" denote "the negative ion detection mode of a liquid chromatograph-mass spectrometer (LC/MS)" and "a temporally early elution mode in the positive ion detection mode of a liquid chromatograph-mass spectrometer (LC/MS)", respectively. In this specification, the "LC/MS pos early" is also simply referred to as "the positive ion detection mode of a liquid chromatograph-mass spectrometer (LC/MS)". In the column "Comments", the structural characteristic of a marker or other information is described.

TABLE 1

| No. | Urinary metabolite ID | Mass | Detection platform | Comments |
|---|---|---|---|---|
| 1 | X-24589 | 321.1556 | LC/MS neg | Structural isomer of X17697 - both are glucuronide of C8H18O2 |
| 2 | X-17697 | 321.1564 | LC/MS neg | Structural isomer of X24589 - both are glucuronide of C8H18O2 |
| 3 | X-18126 | 134.1175 | LC/MS pos early | Good candidate |
| 4 | X-24546 | 231.0509 | LC/MS neg | Sulfated, but otherwise good candidate |
| 5 | X-16567 | 186.1139 | LC/MS neg | Good candidate |
| 6 | X-23511 | 503.1618 | LC/MS neg | On the larger side at ~503 m/z. sometimes this makes structure elucidation more difficult |
| 7 | X-11440 | 246.0744 | LC/MS neg | Disulfated steroid |
| 8 | X-17698 | 389.1825 | LC/MS neg | Glucuronide of C12H22O3 |
| 9 | X-12726 | 233.0129 | LC/MS neg | Glucuronide of C14H26O4 |
| 10 | X-12831 | 433.2088 | LC/MS neg | We think this is something like 3,4-dihydroxyphenylethyl sulfate. |
| 11 | X-12636 | 257.1511 | LC/MS neg | We think this may be methylhexanoyl glutamine. |
| 12 | X-24502 | 208.0966 | LC/MS pos early | We think this may be phenylacetylalanine (not N-acetylphenylalanine, these do not coelute). |
| 13 | X-23787 | 383.1531 | LC/MS neg | Likely isomer of hydroxy DHEA-sulfate |
| 14 | X-21470 | 232.0595 | LC/MS neg | Sulfated |
| 15 | X-24495 | 479.2277 | LC/MS neg | Glucuronides of C19H28O3 |
| 16 | X-15497 | 236.093 | LC/MS neg | C12H15NO4 |
| 17 | X-24473 | 146.0811 | LC/MS pos early | C6H11NO3 |
| 18 | X-17324 | 342.2269 | LC/MS pos early | Several potential formulas |
| 19 | X-22379 | 465.2504 | LC/MS neg | We think this may be androsterone glucuronide |

The urinary markers shown in Table 1 are markers capable of evaluating a cancer by using alone. In the present invention, among the 19 types of metabolites shown in Table 1, at least one type is used as a marker. Incidentally, in this table, as the detection platform, one of the positive ion detection mode of LC/MS and the negative ion detection mode of LC/MS is described, however, there is a case where the positive ion detection mode and the negative ion detection mode can be inverted at a high speed depending on a device to be used, and in such a case, as the detection platform, both the positive ion detection mode and the negative ion detection mode are described.

In one embodiment, as a urinary marker, the metabolite X-18126 shown in Table 1 is measured. That is, a compound measured to have a mass of 134.11 in the positive ion detection mode of LC/MS is measured. More specifically, a compound having the following structure is measured.

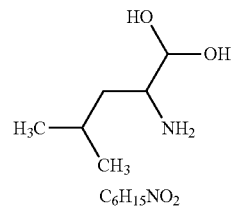

C6H15NO2

In another embodiment, as a urinary marker, the metabolite X-16567 shown in Table 1 is measured. That is, a compound measured to have a mass of 188.12 in the positive ion detection mode of LC/MS and have a mass of 186.11 in the negative ion detection mode of LC/MS is measured. More specifically, a compound having the following structure is measured.

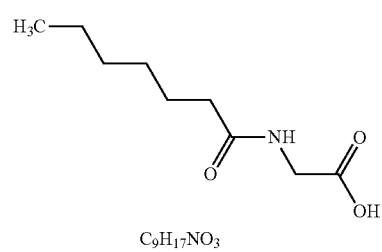

C9H17NO3

In another embodiment, as a urinary marker, the metabolite X-24546 shown in Table 1 is measured. That is, a compound measured to have a mass of 231.05 (divalent ion) in the negative ion detection mode of LC/MS is measured.

In another embodiment, as a urinary marker, the metabolite X-11440 shown in Table 1 is measured. That is, a compound measured to have a mass of 246.07 (divalent ion) in the negative ion detection mode of LC/MS is measured.

In another embodiment, as a urinary marker, the metabolite X-12831 shown in Table 1 is measured. That is, a compound measured to have a mass of 435.22 in the positive ion detection mode of LC/MS and have a mass of 433.20 in the negative ion detection mode of LC/MS is measured.

In still another embodiment, as a urinary marker, the metabolite X-12636 shown in Table 1 is measured. That is, a compound measured to have a mass of 259.16 in the positive ion detection mode of LC/MS and have a mass of 257.15 in the negative ion detection mode of LC/MS is measured.

In still another embodiment, as a urinary marker, the metabolite X-24502 shown in Table 1 is measured. That is, a compound measured to have a mass of 208.09 in the positive ion detection mode of LC/MS and have a mass of 206.08 in the negative ion detection mode of LC/MS is measured.

In still another embodiment, as a urinary marker, the metabolite X-23787 shown in Table 1 is measured. That is, a compound measured to have a mass of 385.16 in the positive ion detection mode of LC/MS and have a mass of 383.15 in the negative ion detection mode of LC/MS is measured.

Incidentally, a mass spectrometer used in the analysis of the metabolites shown in Table 1 has very high resolution and enables the measurement of the mass up to two, three, four, or five decimal places or so. However, in the case where a mass spectrometer having low resolution is used, the measurement of the mass is performed up to an integral number or one decimal place.

According to the present invention, by using at least two urinary markers in combination, more accurate and high-precision cancer evaluation or evaluation of a cancer for specifying the type of the cancer can be performed. For example, 2, 3, 4, 5, 6, 7, 8, 9, 10, 11, 12, 13, 14, 15, 16, 17, 18, or 19 urinary markers shown in Table 1 can be combined. Specifically, measurement may be performed for a combination of the metabolite X-18126 with other metabolite shown in Table 1, for example, but not limited to, a combination of X-18126 with X-16567, a combination of X-18126 with X-24546, a combination of X-18126 with X-11440, a combination of X-18126 with X-12831, a combination of X-18126 with X-12636, a combination of X-18126 with X-24502, a combination of X-18126 with X-23787, a combination of X-16567 with X-11440, a combination of X-16567 with X-24546, a combination of X-16567 with X-12831, a combination of X-16567 with X-12636, a combination of X-16567 with X-24502, a combination of X-16567 with X-23787, a combination of X-18126, X-24546 and X-16567, a combination of X-18126, X-24546 and X-11440, a combination of X-18126, X-24546 and X-12831, a combination of X-18126, X-24546 and X-12636, a combination of X-18126, X-24546 and X-24502, a combination of X-18126, X-24546 and X-23787, a combination of X-18126, X-16567 and X-11440, a combination of X-18126, X-16567 and X-12831, a combination of X-18126, X-16567 and X-12636, a combination of X-18126, X-16567 and X-24502, and a combination of X-18126, X-16567 and X-23787. Further, at least one or more types among 30 types of urinary markers shown in FIG. 5B may be combined. Such a combination can be appropriately selected according to the type of the cancer to be evaluated, the type, gender, and age of a subject, the purpose of evaluation of a cancer, etc.

For example, it is preferred to perform measurement for a combination of X-18126 with X-16567 or a combination of X-18126, X-16567 and X-24546 shown in Table 1, or a combination including these. These metabolites are potent biomarker candidates, and therefore, it becomes possible to distinguish healthy individuals from cancer patients in consideration of these metabolites.

As one example of this distinction method, a principal component analysis which is one type of multivariate analysis can be used. In a metabolite analysis, many metabolites which vary in cancer patients with respect to healthy individuals are found in some cases. If this multidimensional data is used as such, it is difficult to find the characteristics of the data in some cases, and therefore, it is preferred to reduce the multidimensional data to two-dimensional or three-dimensional data so as to visualize the data. Specifically, objective variables (a first principal component and a second principal component) are calculated from a large number of explanatory variables (observed intensities of various metabolites), and each specimen is two-dimensionally plotted and visualized. For example, in FIGS. 9A to 9F, examples of two-dimensionally plotted principal component analysis results are shown. As the multivariate analysis, an analysis method known in this technical field such as a partial least-squares method can also be used.

Figure 5B:
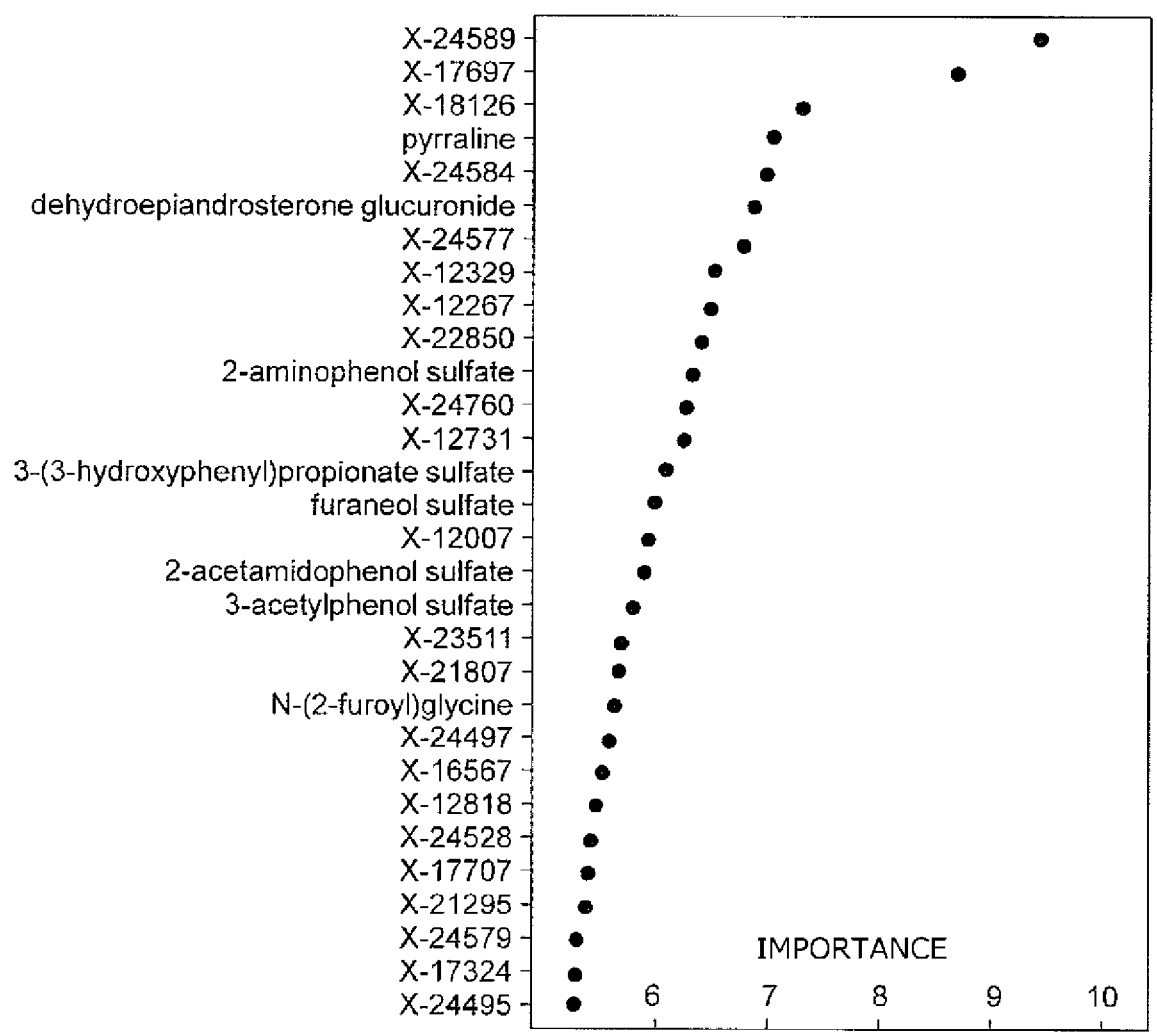
FIG. 5B shows narrowing of biomarker candidate metabolites (including known and unknown structures) by a Random Forest analysis.
Figure 7:
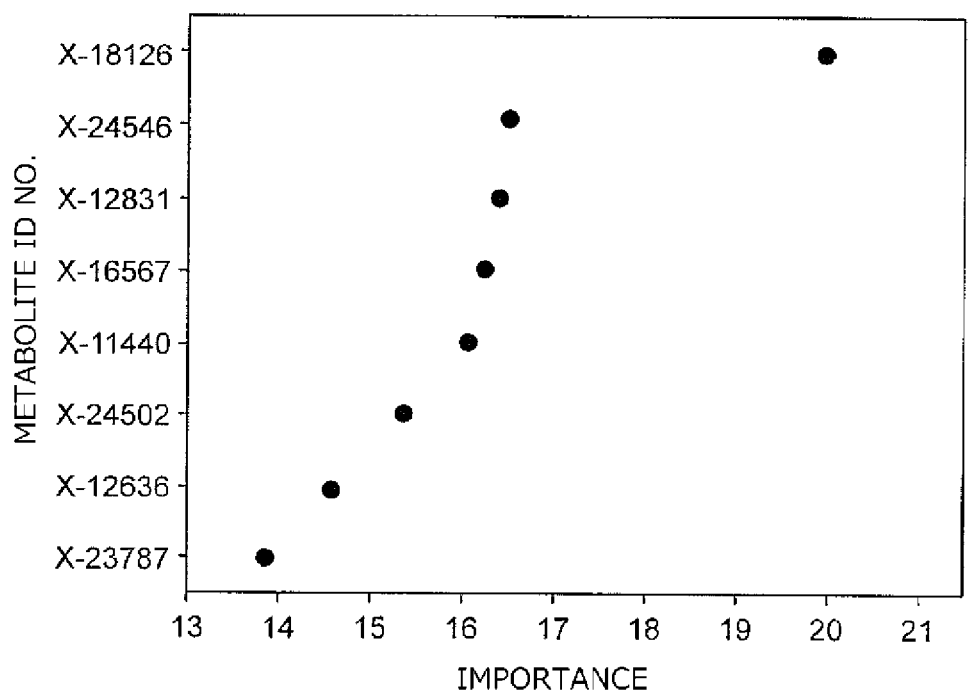
FIG. 7 is a graph showing the importance of urinary marker candidates by a Random Forest analysis.

In a specific embodiment, for example, measurement is performed for the following combinations:

(1) a combination including at least urinary metabolites X-18126 and X-16567;

(2) a combination including at least urinary metabolites X-18126, X-16567, and X-24546;

(3) a combination including 4 to 8 types selected from urinary metabolites X-18126, X-16567, X-24546, X-11440, X-12831, X-12636, X-24502, and X-23787 (FIG. 7);

(4) a combination including 9 to 19 types selected from urinary metabolites X-24589, X-17697, X-18126, X-24546, X-16567, X-23511, X-11440, X-17698, X-12726, X-12831, X-12636, X-24502, X-23787, X-21470, X-24495, X-15497, X-24473, X-17324, and X-22379 (Table 1); and (5) a combination including 20 to 30 types selected from urinary metabolites X-24589, X-17697, X-18126, pyrraline, X-24584, dehydroepiandrosterone glucuronide, X-24577, X-12329, X-12267, X-22850, 2-aminophenol sulfate, X-24760, X-12731, 3-(3-hydroxyphenyl)propionate sulfate, furaneol sulfate, X-12007, 2-acetamidephenol sulfate, 3-acetylphenol sulfate, X-23511, X-21807, N-(2-furoyl)glycine, X-24497, X-16567, X-12818, X-24528, X-17707, X-21295, X-24579, X-17324, and X-24495 (FIG. 5B).

Here, the "cancer" means a disease also called "malignant tumor" or "malignant neoplasm" and is characterized by autonomic growth, invasion, metastasis, and cachexia. The cancer includes primary cancers, metastatic cancers, and recurrent cancers and is classified into stages based on the extent to which a cancer has progressed and spread. A necessary treatment (therapeutic method) also varies depending on this difference among primary cancers, metastatic cancers, and recurrent cancers, or the difference in the stage.

The cancer to be evaluated according to the present invention is not particularly limited, but includes solid cancers (such as breast cancer, colon cancer, lung cancer, prostate cancer, stomach cancer, colorectal cancer, pancreatic cancer, kidney cancer, ovarian cancer, esophageal cancer, liver cancer, biliary tract cancer, bladder cancer, and childhood cancer), sarcomas (such as osteosarcoma and chondrosarcoma), and blood cancers (such as leukemia, malignant lymphoma, and multiple myeloma). In particular, it is preferred to evaluate breast cancer and colon cancer.

The "urine sample" means urine collected from a subject and a sample obtained by treating the urine (for example, urine to which a preservative such as toluene, xylene, hydrochloric acid, or the like is added).

Further, the "subject" is a human and other mammals, for example, a primate (such as a monkey or a chimpanzee), a domestic animal (such as cattle, a horse, a pig, or a sheep), an animal for a pet (such as a dog or a cat), or an experimental animal (such as a mouse, a rat, or a rabbit), and further may be a reptile, a bird, or the like. In particular, the subject may preferably be a human.

The "measurement of a urinary marker" means the measurement of the amount or concentration of a urinary marker in a urine sample, preferably semi-quantitatively or quantitatively, and the amount may be an absolute amount or may be a relative amount. The measurement can be performed directly or indirectly. The direct measurement includes the measurement of the amount or concentration thereof based on a signal which directly correlates with the number of molecules of a urinary metabolite present in a sample. Such a signal is, for example, based on a specific physical or chemical property of the urinary metabolite. The indirect measurement is the measurement of a secondary component (that is, a component other than the urinary metabolite), for example, a signal obtained from a ligand, a label, or an enzymatic reaction product.

In one embodiment of the present invention, a urinary marker, that is, a urinary metabolite is measured. As the measurement method thereof, a method or means known in this technical field can be used, and the method is not particularly limited. For example, the measurement or a urinary marker can be performed by a means for measuring a physical of chemical property specific to a urinary metabolite, for example, a means for measuring an accurate molecular weight or an NMR spectrum, or the like. As the means for measuring a urinary metabolite, analyzers such as a mass spectrometer, an NMR analyzer, a two-dimensional electrophoresis device, a chromatograph, and a liquid chromatograph-mass spectrometer are exemplified. A urinary marker may be measured using these analyzers alone, but may be measured using a plurality of analyzers.

The urinary metabolites shown in Table 1 were found by a liquid chromatograph-mass spectrometer, and therefore, by using a liquid chromatograph-mass spectrometer, these metabolites can be measured.

A urinary marker contained in a urine sample collected from a subject is measured as described above, and a cancer in the subject can be evaluated based on the results. Further, a urinary marker in urine samples collected from a subject at a plurality of time points may be measured.

By the method for evaluating a cancer of the present invention, the presence or progression of a cancer can be determined early. That is, the presence or absence of a cancer at an initial stage which is not recognized by a currently available diagnostic method or criteria can be determined, or a cancer malignancy or prognosis can be predicted. Therefore, a subject can receive a treatment of the cancer early or can receive a treatment suitable for a specific malignancy or the like. In addition, since a urine sample is used, the method has low invasiveness and also has an advantage that a cancer can be evaluated simply and at low cost.

The method for evaluating a cancer of the present invention can be performed easily and simply by using a kit and/or a device comprising a means for measuring a urinary marker (urinary metabolite).

The kit for evaluating a cancer according to the present invention comprises at least the following means:

a means for measuring a urinary metabolite in a urine sample, preferably, a urinary metabolite shown in the above Table 1.

One example of the kit of the present invention is a reagent set for mass spectrometry and is constituted by, for example, an isotope labeling reagent, a fractionating mini-column, a buffer solution, and the like. The kit of the present invention may also include an instruction describing a procedure and a protocol for performing the method of the present invention, a table showing a reference or a reference range to be used in the evaluation of a cancer, or the like.

The components contained in the kit of the present invention may be provided separately or may be provided in a single container. Preferably, the kit of the present invention contains all the necessary components for performing the method of the present invention such that the components can be used immediately, for example, as the components at adjusted concentrations.

The device for evaluating a cancer according to the present invention comprises the following means:

a measurement section which is configured to measure a urinary metabolite in a urine sample, preferably a urinary metabolite shown in the above Table 1;

a comparison section which is configured to compare the measured value of the urinary metabolite measured by the measurement section with a reference or a previously measured value; and a determination section which is configured to evaluate a cancer based on the comparison results obtained by the comparison section.

Further, in the case where a multivariate analysis is used, the device for evaluating a cancer according to the present invention comprises the following means:

a measurement section which is configured to measure a urinary metabolite in a urine sample, preferably a urinary metabolite shown in the above Table 1;

a comparison section which is configured to compare the calculated value of an objective variable (such as a first principal component or a second principal component) obtained by a multivariate analysis from an explanatory variable (the amount or concentration of a urinary metabolite or the ratio of observed ion intensities of a metabolite which has increased or decreased in a cancer patient with respect to a healthy individual) measured by the measurement section with a reference or a previously calculated value of the objective variable; and a determination section which is configured to evaluate a cancer based on the comparison results obtained by the comparison section.

The device of the present invention may preferably be a system in which the above-mentioned measurement section, comparison section, and determination section are operatively connected with one another so that the method of the present invention can be performed. One embodiment of the device of the present invention is shown in FIG. 1.

Here, the measurement section includes a means for measuring a urinary metabolite in a urine sample as described above, and is provided with, for example, an analyzer such as a mass spectrometer, an NMR analyzer, a two-dimensional electrophoresis device, a chromatograph, or a liquid chromatograph-mass spectrometer.

The measurement section includes a data analysis section composed of a software and a calculating machine for processing a measured value obtained from an analyzer as described above or the like. The data analysis section may calculate the amount or concentration of a urinary metabolite contained in a urine sample by referring to data such as a calibration curve based on the measured value obtained from an analyzer as described above or the like. On the other hand, in the case where a multivariate analysis is used, the data analysis section may calculate an objective variable (such as a first principal component or a second principal component) obtained by a multivariate analysis from an explanatory variable (the amount or concentration of a urinary metabolite or the ratio of observed ion intensities of a metabolite which has increased or decreased in a cancer patient with respect to a healthy individual). The data analysis section may include, for example, a signal display part, a unit for analyzing a measured value, a computer unit, or the like.

Further, the comparison section may read out a reference associated with the amount or concentration of the urinary metabolite from a memory device (database) or the like and compare the measured value of the urinary metabolite measured by the above-mentioned measurement section with the reference. On the other hand, in the case where a multivariate analysis is used, the comparison section may read out the reference of an objective variable (for example, a first principal component) from a memory device (database) or the like and compare the calculated value of the objective variable obtained by the above-mentioned measurement section with the reference. At this time, the comparison section may select and read out an appropriate reference according to the type of the urinary marker. Alternatively, in the case of monitoring over time in the same subject, the comparison section may read out a previously measured value from a memory device (database) or the like and compare it with the measured value of the urinary metabolite measured by the measurement section.

Further, the determination section may evaluate a cancer based on the results of comparison of the measured value of the urinary metabolite with the reference in the comparison section or based on the results of comparison of the measured values of the urinary metabolite at a plurality of time points in the comparison section. On the other hand, in the case where a multivariate analysis is used, the determination section may evaluate a cancer based on the results of comparison of the calculated value of the objective variable with the reference in the comparison section or based on the results of comparison of the calculated values of the objective variable at a plurality of time points in the comparison section. Here, the determination section may acquire information indicating the presence of a cancer, the stage of a cancer, or the like in the subject. A preferred device may be a device which can be used without knowledge of a specialized clinician, and for example, there is an electronic device into which a sample is simply added.

The device of the present invention may further comprise a data storage section, a data output/display section, or the like.

In this specification, the "evaluation of a cancer" includes detection of a cancer in a subject, prediction of a cancer risk in a subject, determination of a cancer stage in a subject, determination of a cancer prognosis in a subject, and evaluation of the effect of a treatment on a cancer present in a subject. Since a treatment to be applied varies depending on a cancer malignancy, for example, a stage or a prognosis (such as metastasis or recurrence), it is important to determine a cancer stage or prognosis. Further, the "evaluation" in the present invention also includes continuous monitoring of a cancer having already been evaluated or diagnosed and confirmation of evaluation or diagnosis of a cancer having already been performed.

Incidentally, the "evaluation" by the method, the kit, and the device for evaluating a cancer according to the present invention is meant that a subject can be evaluated at a statistically significant level. Therefore, the "evaluation" by the method, the kit, and the device for evaluating a cancer according to the present invention also includes a case where correct results are not always obtained for all the evaluation subjects (that is, 100%). The statistically significant level can be determined using various known statistical evaluation tools, for example, determination of a confidence interval, determination of a p value, a Student t test, a Mann-Whitney test, and the like. A preferred confidence interval may be at least 90%. The p value may preferably be 0.1, 0.01, 0.005, or 0.0001. More preferably, at least 60%, at least 80%, or at least 90% of the subjects can be appropriately evaluated by the method, the kit, and the device for evaluating a cancer according to the present invention.

A specific example of the evaluation of a cancer is as follows. In one embodiment, a urinary marker (urinary metabolite) in a urine sample of a subject is measured, and the measured value and a reference are compared.

The reference is the amount or concentration of a urinary metabolite to serve as an index of the presence of a specific cancer or a range of the amount or concentration thereof. On the other hand, in the case where a multivariate analysis is used, the calculated value of an objective variable for distinguishing healthy individuals from cancer patients may be a reference. For example, the reference can be derived from healthy individuals (a group) or individuals with a low cancer risk (a group). Alternatively, the reference can be derived from patients (a group of patients) having a specific cancer or having a cancer at a known stage or having a cancer with a specific prognosis. The reference to be applied to an individual subject can vary depending on various physiological parameters such as the type, age, and gender of a subject animal.

Preferably, a correlation between the amount or concentration of a urinary marker and the presence of a specific cancer and/or a specific cancer stage or prognosis is recorded as a database. Then, the measured value of the urinary marker in a urine sample can be compared with the reference in the database. Such a database is useful as a reference or a reference range to serve as an index of the presence or absence of a specific cancer or a specific cancer stage or prognosis.

The urinary metabolites shown in Table 1 have a difference in the amount or concentration between cancer patients and healthy individuals, and the amount or concentration thereof varies depending on the presence of a cancer (particularly, colon cancer and/or breast cancer). For example, among the urinary markers shown in Table 1, the amount or concentration of each of X-18126, X-12831, and X-24502 decreases in cancer patients as compared with those of healthy individuals, and the amount or concentration of each of X-24546, X-16567, X-11440, X-12636, and X-23787 increases in cancer patients.

Therefore, when the reference is derived from healthy individuals (a group) or individuals with a low cancer risk (a group), a case where the amount or concentration of the urinary metabolite (X-18126, X-12831, or X-24502) shown in Table 1 is equivalent to or higher than the reference indicates that there is a low possibility that a subject has developed a cancer (particularly colon cancer and/or breast cancer), and a case where the amount or concentration is lower than the reference indicates that there is a high possibility that a subject has developed a cancer (particularly colon cancer and/or breast cancer). On the other hand, a case where the amount or concentration of the urinary metabolite (X-24546, X-16567, X-11440, X-12636, or X-23787) shown in Table 1 is equivalent to or lower than the reference indicates that there is a low possibility that a subject has developed a cancer (particularly colon cancer and/or breast cancer), and a case where the amount or concentration is higher than the reference indicates that there is a high possibility that a subject has developed a cancer (particularly colon cancer and/or breast cancer).

Further, it is also possible to perform determination using a first principal component, a second principal component, or the like by performing a principal component analysis using the plurality of urinary markers. For example, in the case where 8 types of urinary markers are used, results of principal component analysis as shown in FIG. 9C may be obtained. It is found that healthy individuals and cancer patients (colon cancer and breast cancer) can be distinguished by the calculated value of the first principal component (for example, a straight line on which the first principal component passes through −1). In the case of FIG. 9C, a case where the value of the first principal component is −1 or larger falls under a cancer patient zone, and a case where the value is smaller than −1 falls under a healthy individual zone. That is, in the case of a new subject, whether the subject is healthy or there is a high possibility that the subject has developed a cancer can be found depending on whether the calculated value of the first principal component of the subject is in the healthy individual zone or in the cancer patient zone.

On the other hand, when the reference is derived from patients (a group of patients) having a specific cancer or having a cancer at a known stage or having a cancer with a specific prognosis, a case where it is determined that the amount or concentration of a urinary marker is equivalent to the reference or shows no significant difference from the reference (or in the case of X-18126, X-12831, or X-24502, the amount or concentration is lower than the reference, or in the case of X-24546, X-16567, X-11440, X-12636, or X-23787, the amount or concentration is higher than the reference) indicates that there is a high possibility that the subject has developed the specific cancer, or there is a high possibility that the subject has developed the cancer at the known stage, or there is a high possibility that the subject has the specific prognosis.

Further, it is also possible to perform determination using a first principal component, a second principal component, or the like by performing a principal component analysis using the plurality of urinary markers. For example, in the case where 8 types of urinary markers are used, results of principal component analysis as shown in FIG. 9C may be obtained. It is found that healthy individuals and cancer patients (colon cancer and breast cancer) can be distinguished by the calculated value of the first principal component (for example, a straight line on which the first principal component passes through −1). That is, in the case of a new subject, a case where the calculated value of the first principal component is in the cancer patient zone indicates that there is a high possibility that the subject has developed the specific cancer, or there is a high possibility that the subject has developed the cancer at the known stage, or there is a high possibility that the subject has the specific prognosis.

In another embodiment, a urinary sample is collected from a subject at a plurality of time points, a urinary marker contained in the urinary sample at each time point is measured, and the measured values of the urinary marker are compared at the respective time points. More specifically, the amount or concentration (a) of the urinary marker at the first time point and the amount or concentration (b) of the urinary marker at the second time point are compared. In the case where a principal component analysis is performed, for example, the calculated value of the first principal component at the first time point and the calculated value thereof at the second time point are compared. The measurement can be performed over time at least 2 times, 3 times, 4 times, 5 times, 10 times, 15 times, 20 times, 30 times, or more than 30 times at an interval of, for example, 1 day, 2 days, 5 days, 1 week, 2 weeks, 3 weeks, 1 month, 2 months, 3 months, a half year, 1 year, 2 years, 3 years, 5 years, or more than 5 years. By this comparison, monitoring over time can be performed, and cancer progression, cancer metastasis or recurrence, or the like can be evaluated.

To be more specific, with respect to the urinary marker (X-18126, X-12831, or X-24502), a case where the ratio (b/a) between the amount or concentration (a) of the urinary marker measured at the first time point and the amount or concentration (b) of the urinary marker measured at the second time point is smaller than 1, preferably a case where the ratio continuously shows a value smaller than 1 indicates that there is a high possibility that the cancer of the subject has further progressed. With respect to the urinary marker (X-24546, X-16567, X-11440, X-12636, or X-23787), a case where the ratio (b/a) between the amount or concentration (a) of the urinary marker measured at the first time point and the amount or concentration (b) of the urinary marker measured at the second time point exceeds 1, preferably a case where the ratio continuously shows a value exceeding 1 indicates that there is a high possibility that the cancer of the subject has further progressed.

On the other hand, with respect to the urinary marker (X-18126, X-12831, or X-24502), for example, a case where the ratio (b/a) between the amount or concentration (a) of the urinary marker measured at the first time point and the amount or concentration (b) of the urinary marker measured at the second time point exceeds 1, preferably a case where the ratio continuously shows a value exceeding 1 indicates that there is a high possibility that the cancer of the subject has remitted or has been reduced. Further, with respect to the urinary marker (X-24546, X-16567, X-11440, X-12636, or X-23787), a case where the ratio (b/a) between the amount or concentration (a) of the urinary marker measured at the first time point and the amount or concentration (b) of the urinary marker measured at the second time point is smaller than 1, preferably a case where the ratio continuously shows a value smaller than 1 indicates that there is a high possibility that the cancer of the subject has remitted or has been reduced.

Further, the method for evaluating a cancer may be performed in combination with other conventionally known methods for diagnosing a cancer. Such known methods for diagnosing a cancer may include measurement of a cancer marker in blood, imaging examination, for example, ultrasound examination, computed tomography (CT), X-ray examination, magnetic resonance imaging (MRI), positron CT (PET), and the like, endoscopy, and pathological examination using biopsy.

Based on the above-mentioned evaluation results, a medical doctor makes a diagnosis of a cancer of a subject and can provide an appropriate treatment. That is, the present invention also relates to a method for evaluating and treating a cancer in a subject. For example, a cancer in a subject is evaluated according to the method for evaluating a cancer according to the present invention, and in the case where it is evaluated that there is a high possibility that the subject has developed a cancer, a treatment to cure the cancer or prevent the progression of the cancer may be performed in the subject. Further, in the case where it is evaluated that there is a high possibility that the stage of the cancer in the subject has progressed or the cancer prognosis is poor, the treatment may be continued, or if necessary, the change of the therapeutic method may be considered. Alternatively, in the case where it is evaluated that there is a high possibility that a cancer is present in the subject, the presence of the cancer may be confirmed by performing other methods for diagnosing a cancer as described above.

For a cancer, surgery, radiation therapy, chemotherapy, immunotherapy, and the like can be performed alone or in combination as appropriate. The treatment of a cancer can be appropriately selected by a person skilled in the art in consideration of the type, stage, or malignancy of the cancer, the gender, age, and conditions of a patient, the responsiveness of the patient to the treatment, or the like.

Figure 27:
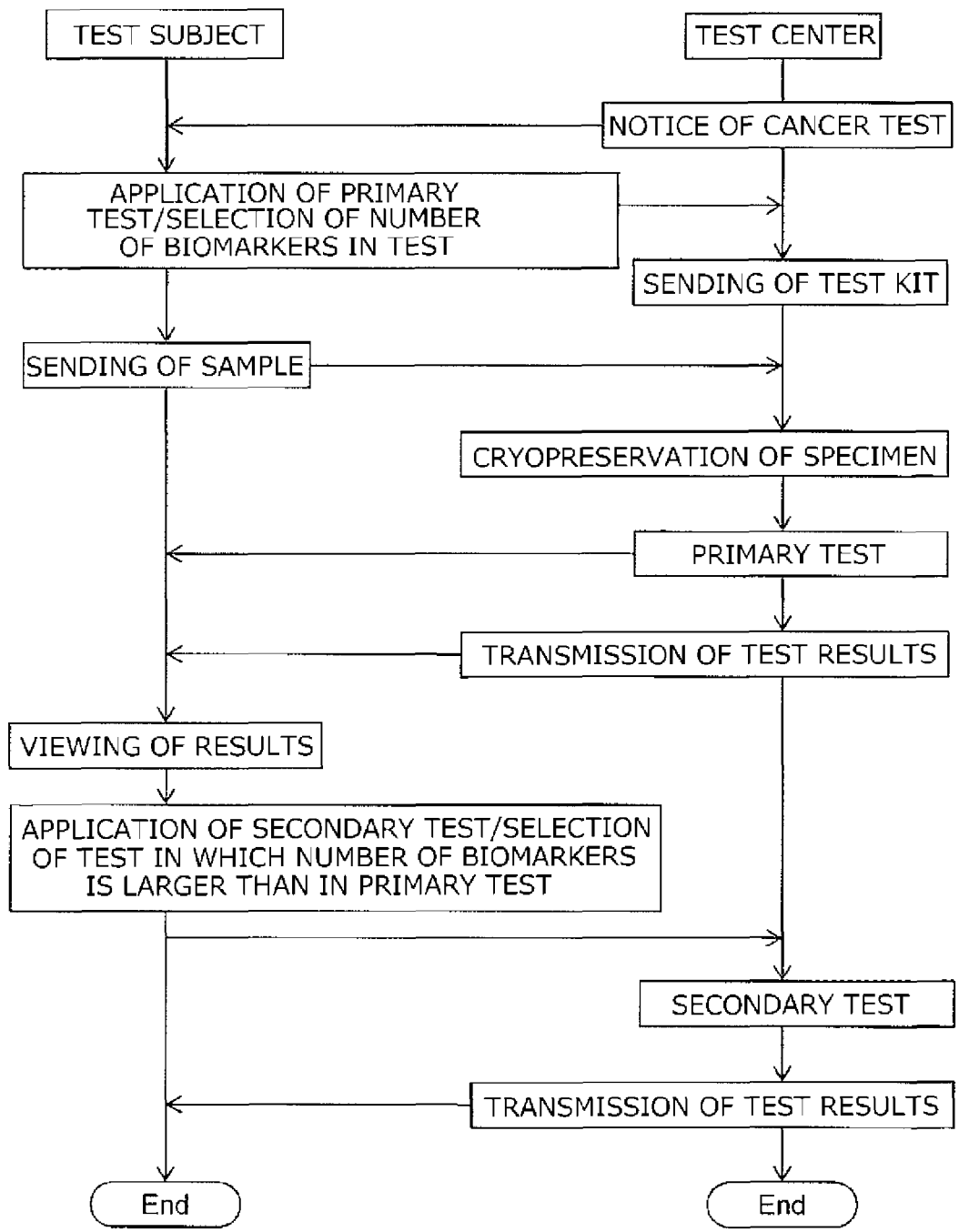
FIG. 27 shows one example of a flow between a test subject and a test center.

As an example of applying the present invention, a cancer test in a test center will be described. FIG. 27 shows one example of a flow between a test subject and a test center. In the test center, a notice of the cancer test is provided according to a request or the like of the test subject. The test subject may select the number of biomarkers in the test in the application of a primary test. For example, as the number of biomarkers, two types or three types of metabolites (for example, the urinary metabolites X-18126 and X-16567, or X-18126, X-16567 and X-24546) can be exemplified. This can be utilized as an all-cancer test (various cancers are analyzed at one time).

Subsequently, the test center provides a test kit necessary for collecting urine to the test subject. According to need, the kit is sent by mail or the like. After receiving the test kit, the test subject provides a specimen to the test center or performs sending or the like of the specimen. In the test center, the specimen is cryopreserved at about −80° C. according to need for the subsequent test. In the test center, a primary test is performed, and the test results is sent to the test subject.

The test subject receives the results of the primary test and applies a secondary test according to the contents. The secondary test is a test in which the number of biomarkers is larger than in the primary test. This is a test capable of specifying up to a cancer site and a cancer type. For example, a test by 8 types of metabolites, 19 types of metabolites, 30 types of metabolites, or more than 30 types of metabolites is selected. Here, 4 to 7 types of metabolites including X-18126 and X-16567 may be selected from 8 types of metabolites shown in FIG. 7B, 9 to 18 types of metabolites including X-18126 and X-16567 may be selected from 19 types of metabolites shown in Table 1, 20 to 29 types of metabolites including X-18126 and X-16567 may be selected from 30 types of metabolites shown in FIG. 5B, or 31 or more types of metabolites including X-18126 and X-16567 may be selected from the metabolites shown in this specification. After the secondary test, a third test or a fourth test in which the number of metabolites is further larger may be performed. The test results are sent or transmitted to the test subject.

Figure 28:
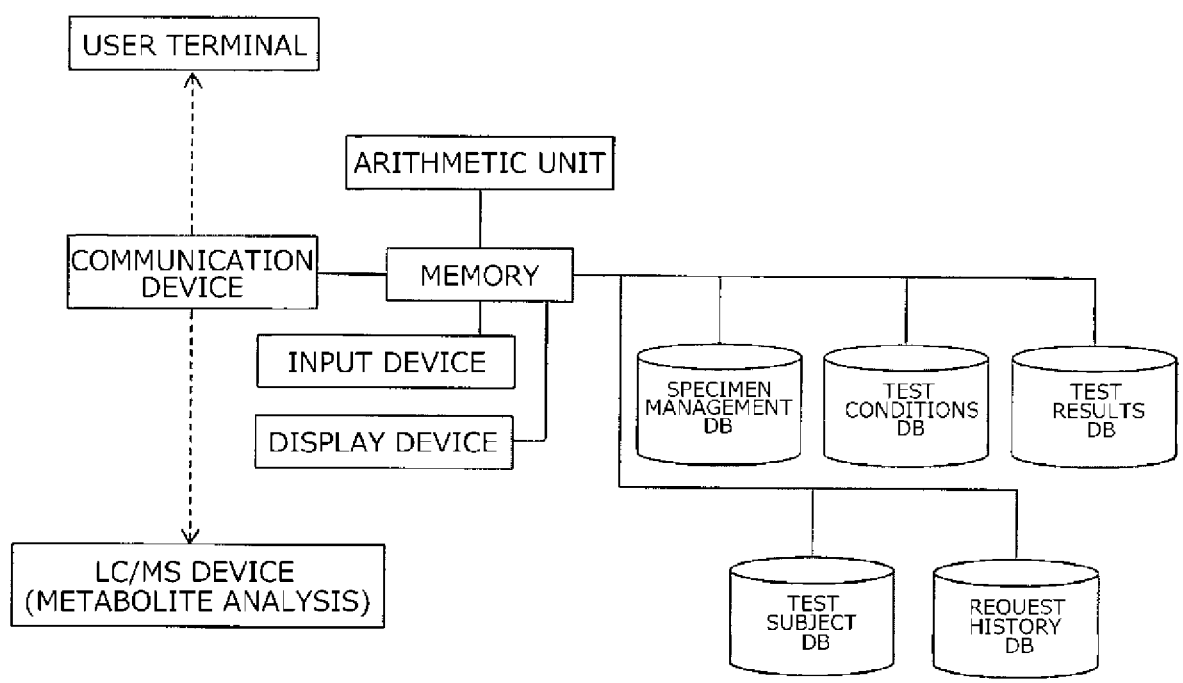
FIG. 28 shows a configuration example of a system for performing the flow shown in FIG. 27.

FIG. 28 shows a system for performing the flow shown in FIG. 27. A method for exchanging information with a test center or an organization which manages information from the test center by the test subject may include exchange through a terminal and a communication device.

The test center or the organization which manages information from the test center has a terminal including a memory, an arithmetic unit, an input device, and a display device, a DB for managing a specimen, a DB in which test conditions are stored, a DB in which test results are stored, a DB in which the information of a test subject is stored, and a DB in which a test request history is stored. An LC/MS device necessary for the test may be connected so that data can be exchanged therewith.

In the terminal on the user side, a screen for inputting the information of a patient necessary for the test, a screen for selecting the number of metabolites to be examined in the primary test and the subsequent test (or a screen for selecting a menu in which the number of metabolites is different), and an output screen for receiving and displaying the test results are provided.

The method for testing a cancer using the system will be described. A step of receiving an input of the selection of a urinary metabolite to be used in a test as a primary test or the number of urinary metabolites (or a menu in which the number of urinary metabolites is different), a step of performing a multivariate analysis of the measured value in a urine sample (specimen) with respect to the input urinary metabolite or the input number of urinary metabolites (or the urinary metabolites corresponding to the menu), a step of storing test results of the multivariate analysis, and a step of outputting the test results as primary test results are included. Here, in the selection of the urinary metabolite or the number of urinary metabolites (or the menu in which the number of metabolites is different), the selection may be performed from 2 types of metabolites (X-18126 and X-16567), 3 types of metabolites (X-18126, X-16567, and X-24546), 4 to 8 types of metabolites including X-18126 and/or X-16567, 9 to 19 types of metabolites including X-18126 and/or X-16567, and 20 to 30 types of metabolites including X-18126 and/or X-16567. As the multivariate analysis, a known analysis method including a principal component analysis and a partial least-squares method can be used.

Further, in the case where a test subject is suspected of having a cancer from the results of the primary test, a step of receiving an input of a larger number of urinary metabolites than in the primary test as a secondary test may be further included. According to this, it becomes possible to confirm the suspicion of a cancer in the primary test and further to specify a cancer site and/or a cancer type.

Further, by using a urinary marker to be used in the present invention, the effectiveness of a treatment (therapeutic agent or therapeutic method) on a cancer, particularly colon cancer and breast cancer may be evaluated, or a candidate of a therapeutic agent for a cancer can be screened. Specifically, a method for evaluating the effectiveness of a treatment on a cancer or a method for screening a candidate of a therapeutic agent for a cancer includes:

(a) measuring a urinary metabolite in a urine sample from an animal having a cancer and having received a treatment with a test therapeutic agent or a test therapeutic method; and (b) evaluating the effectiveness of the test therapeutic agent or the test therapeutic method on a cancer based on the measurement results in (a).

In the method of the present invention, a urine sample is collected from an animal having a cancer, that is, an animal having developed a cancer or having a risk of developing a cancer, and a urinary marker in the urine sample is measured. Preferably, a urine sample may be collected from an animal having a cancer before a treatment with a test therapeutic agent or a test therapeutic method, and a urinary marker in the urine sample may be measured. After the treatment with the test therapeutic agent or the test therapeutic method is performed for the animal having a cancer, a urine sample may be collected at an appropriate time and a urinary marker in the urine sample may be measured. The urine sample may be collected, for example, immediately after the treatment, after 30 minutes, after 1 hour, after 3 hours, after 5 hours, after 10 hours, after 15 hours, after 20 hours, after 24 hours (1 day), after 2 to 10 days, after 10 to 20 days, after 20 to 30 days, or after 1 month to 6 months. The measurement of the urinary marker in the urine sample and the evaluation of a cancer can be performed in the same manner as described above.

The target animal may be a human having a cancer or may be a cancer model animal (such as a mouse, a rat, or a rabbit). In general, after the effectiveness of a test therapeutic agent or a test therapeutic method is confirmed in a model animal, the effectiveness is evaluated in, for example, a clinical test or the like in a human.

The type of the test therapeutic agent or the test therapeutic method to be evaluated or screened is not particularly limited. For example, the test therapeutic agent or the test therapeutic method may include any material factors, specifically, a naturally occurring molecule, for example, an amino acid, a peptide, an oligopeptide, a polypeptide, a protein, a nucleic acid, a lipid, a carbohydrate (such as a sugar), a steroid, a glycopeptide, a glycoprotein, a proteoglycan, or the like; a synthetic analog or a derivative of a naturally occurring molecule, for example, a peptide mimetic, a nucleic acid molecule (such as an aptamer, an antisense nucleic acid, or a double-stranded RNA (RNAi)) or the like; a non-naturally occurring molecule, for example, a low-molecular weight organic compound (such as an inorganic and organic compound library or a combinatorial library), or the like; and a mixture thereof. Further, the therapeutic agent or the therapeutic method may be a single substance or may be a complex composed of a plurality of substances, a food, a feed, or the like. Further, the therapeutic agent or the therapeutic method may be a radiation, an ultraviolet ray, or the like in addition to the material factors as described above.

The treatment of an animal with the test therapeutic agent or the test therapeutic method may vary depending on the type of the therapeutic agent or the therapeutic method, but can be determined easily by a person skilled in the art. For example, administration conditions such as a dose, an administration period, and an administration route of the test therapeutic agent can be appropriately determined by a person skilled in the art.

Further, the effectiveness of the test therapeutic agent or the test therapeutic method can also be examined under several conditions. Such conditions may include a time or period, an amount (large or small), a frequency, and the like for the treatment with the test therapeutic agent or the test therapeutic method. For example, a plurality of doses can be set by preparing a dilution series of the test therapeutic agent, or the like.

Further, in the case where the additive effect, the synergistic effect, or the like of a plurality of test therapeutic agents or test therapeutic methods is examined, therapeutic agents or therapeutic methods may be used in combination.

It is possible to evaluate whether or not the test therapeutic agent or the test therapeutic method is effective in elimination of a cancer, reduction of a cancer, improvement of symptoms caused by a cancer, or arrest or slow of the progression of a cancer by measuring a urinary marker in a urine sample collected from an animal after a treatment with the test therapeutic agent or the test therapeutic method, and comparing the measured value with the amount or concentration before the treatment.

For example, the amount or concentration of each of the urinary metabolites X-18126, X-12831, and X-24502 decreases in cancer patients as compared with those of healthy individuals. Therefore, with respect to the urinary metabolite X-18126, X-12831, or X-24502, a case where the measured value after the treatment is higher than the measured value before the treatment indicates that the test therapeutic agent or the test therapeutic method is effective in elimination of a cancer, reduction of a cancer, improvement of symptoms caused by a cancer, or arrest or slow of the progression of a cancer. On the other hand, a case where the measured value after the treatment is lower than the measured value before the treatment or shows no significant difference from the measured value before the treatment indicates that the test therapeutic agent or the test therapeutic method is not effective in the treatment of a cancer.

Further, for example, the amount or concentration of each of the urinary metabolites X-24546, X-16567, X-11440, X-12636, and X-23787 increases in cancer patients. Therefore, with respect to the urinary metabolite X-24546, X-16567, X-11440, X-12636, or X-23787, a case where the measured value after the treatment is lower than the measured value before the treatment indicates that the test therapeutic agent or the test therapeutic method is effective in elimination of a cancer, reduction of a cancer, improvement of symptoms caused by a cancer, or arrest or slow of the progression of a cancer. On the other hand, a case where the measured value after the treatment is higher than the measured value before the treatment or shows no significant difference from the measured value before the treatment indicates that the test therapeutic agent or the test therapeutic method is not effective in the treatment of a cancer.

Further, it is also possible to perform determination using a first principal component, a second principal component, or the like by performing a principal component analysis using the plurality of urinary markers. For example, in the case where 8 types of urinary markers are used, results of principal component analysis as shown in FIG. 9C are obtained. However, it is found that healthy individuals and cancer patients (colon cancer and breast cancer) can be distinguished by the calculated value of the first principal component (for example, a straight line on which the first principal component passes through −1). That is, in the case of a new subject, it is found that the test therapeutic agent or the test therapeutic method is effective in elimination of a cancer, reduction of a cancer, improvement of symptoms caused by a cancer, or arrest or slow of the progression of a cancer by a shift of the calculated value of the first principal component of the subject from the cancer patient zone to the healthy individual zone. On the other hand, a case where the calculated value of the first principal component remains in the cancer patient zone indicates that the test therapeutic agent or the test therapeutic method is not effective in the treatment of a cancer.

Accordingly, by the method for evaluating the effectiveness of a treatment on a cancer according to the present invention, a therapeutic agent or a therapeutic method for treating or preventing a cancer can be found, and moreover, the effectiveness of the therapeutic agent or the therapeutic method can be confirmed.

Hereinafter, the present invention will be specifically described by presenting Examples; however, the Examples are merely provided for explaining the present invention, and do not limit or restrict the scope of the invention disclosed in this application.

EXAMPLES

Example 1: Regarding Comprehensive Analysis Scheme for Urinary Metabolites

Figure 2:
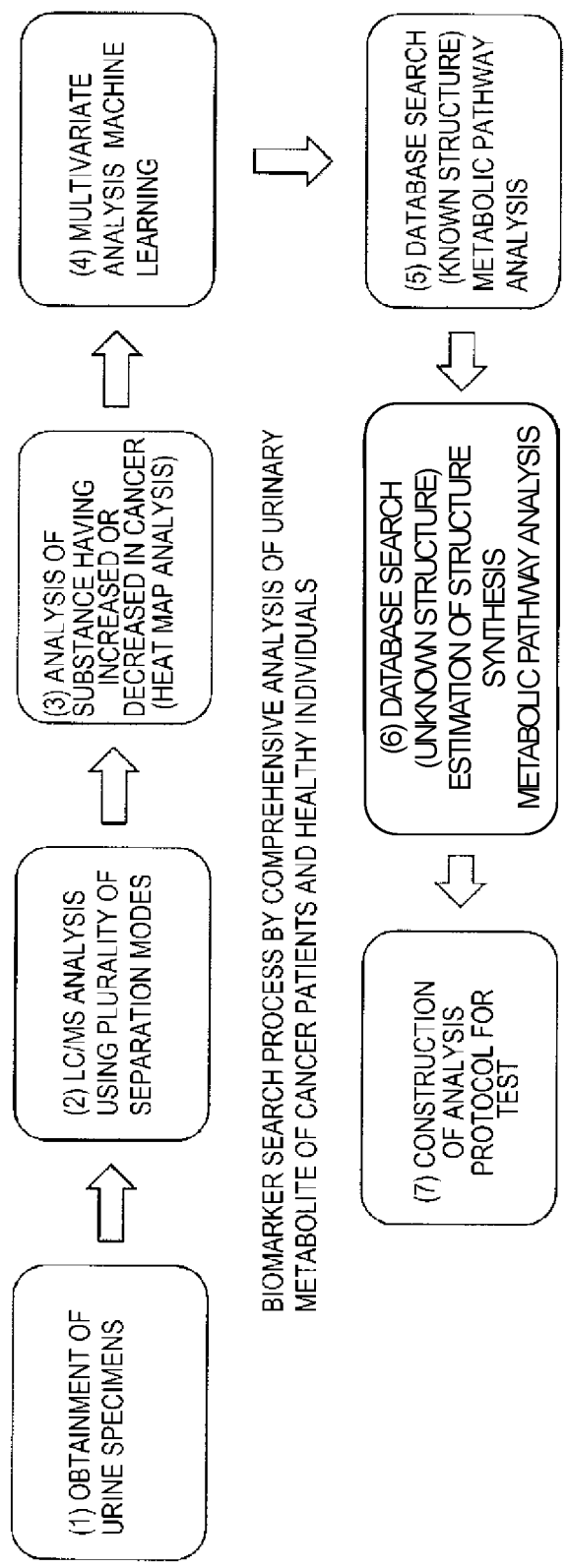
FIG. 2 shows a comprehensive analysis scheme for urinary metabolites.

In FIG. 2, a comprehensive analysis scheme performed this time is shown. Basically, the following processes are included.

(1) A plurality of urine specimens including additional clinical information are obtained as the urine specimens of healthy individuals and cancer patients.

(2) With respect to the obtained urine specimens, a comprehensive analysis is performed by a liquid chromatograph-mass spectrometer (LC/MS) using a plurality of separation modes. In order to classify the urine of healthy individuals and cancer patients from data obtained by LC/MS in the end, as many metabolites as possible are detected.

(3) A Heat map analysis for sorting components having increased or decreased in the urine of cancer patients with respect to components detected in the urine of healthy individuals is performed.

(4) A principal component analysis which is one type of multivariate analysis is performed based on the results of the Heat map analysis, and conditions capable of distinguishing healthy individuals from cancer patients are searched for. That is, a plurality of metabolites to be biomarker candidates are specified, 2 or 3 new concept variables are introduced by a principal component analysis, and conditions for distinguishing healthy individuals from cancer patients are examined. With respect to the results of the principal component analysis, a Random Forest method which is one type of machine learning is applied, and the degree of contribution of each metabolite component is evaluated.

(5) In the case where it is found that the component is a substance with a known structure based on the results of database search, a metabolic pathway analysis of the substance is performed. If it is valid, the substance can be a biomarker candidate.

(6) In the case where it is found that the structure of the component is unknown by database search, the structure is estimated from the obtained MS spectrum or MS/MS spectrum. In the end, a candidate substance whose structure is estimated is synthesized, and whether or not the MS spectrum, the MS/MS spectrum, or the like coincides with the analysis results is confirmed. In the case where it coincides with the results, the component can be a biomarker candidate after a metabolic pathway analysis is performed.

(7) Based on the above results, a final analysis protocol for a test including biomarker candidates is determined.

Example 2: Collection of Urine Specimens

There are several methods for obtaining urine specimens necessary for the analysis.

(1) Urine specimens of healthy individuals and cancer patients are obtained from a medical institution with the approval of the ethics committee. At this time, additional clinical information (such as gender, age, body height, body weight, BMI, the presence or absence of a cancer, and in the case where a cancer is present, the cancer stage) is provided from a medical worker. In this case, it may take a lot of time to collect a necessary number of specimens.

(2) Urine specimens of healthy individuals and cancer patients including additional clinical information are purchased from a biobank company. In this case, ethical approval is not needed; however, there is no biobank company in Japan, and therefore, the specimens are derived from foreigners.

The number of specimens this time was set as follows: 15 healthy individuals and cancer patients (15 colon cancer patients and 15 breast cancer patients), and the method (2) was adopted for largely shortening the time for obtaining the specimens. Specifically, cryopreserved specimens (about 10 mL per specimen) were obtained from a German biobank company, Indivumed GmbH and a US biobank company, BioOptions, Inc.

Example 3: LC/MS Analysis in Plurality of Separation Modes

In order to comprehensively analyze urinary metabolites, a liquid chromatograph/mass spectrometer (LC/MS) is most suitable. As an ionization method in MS, positive and negative ionization modes (+ESI mode/−ESI mode) of an electrospray ionization (ESI) method are used, and in addition thereto, in order to obtain structure information, mass spectrometry/mass spectrometry (MS/MS) is used, and thus, the selection of the separation mode in LC is an object to be solved. However, the separation mode cannot be limited to one separation mode at a stage where the urinary metabolite is unknown, and therefore, as shown in the following Table 2, it was determined to use a plurality of separation modes.

TABLE 2

Analysis Mode Used in Urinary Metabolite Analysis

| Mode | Separation mode | Ionization mode | Mass spectrometry mode | Abbreviation |
| --- | --- | --- | --- | --- |
| Analysis mode 1 | Reverse phase mode (ODS1) | +ESI mode | MS/MS mode | HPLC(ODS1)-MS/MS (+ESI) |
| Analysis mode 2 | Reverse phase mode (ODS2) | +ESI mode | MS/MS mode | HPLC(ODS2)-MS/MS (+ESI) |
| Analysis mode 3 | Reverse phase mode (ODS1) | −ESI mode | MS/MS mode | HPLC(ODS1)-MS/MS (−ESI) |
| Analysis mode 4 | Normal phase mode (HILIC) | +ESI mode | MS/MS mode | HPLC(HILIC)-MS/MS (+ESI) |

Example 4: Heat Map Analysis (Identification of Metabolite Having Increased or Decreased in Cancer)

Figure 3:
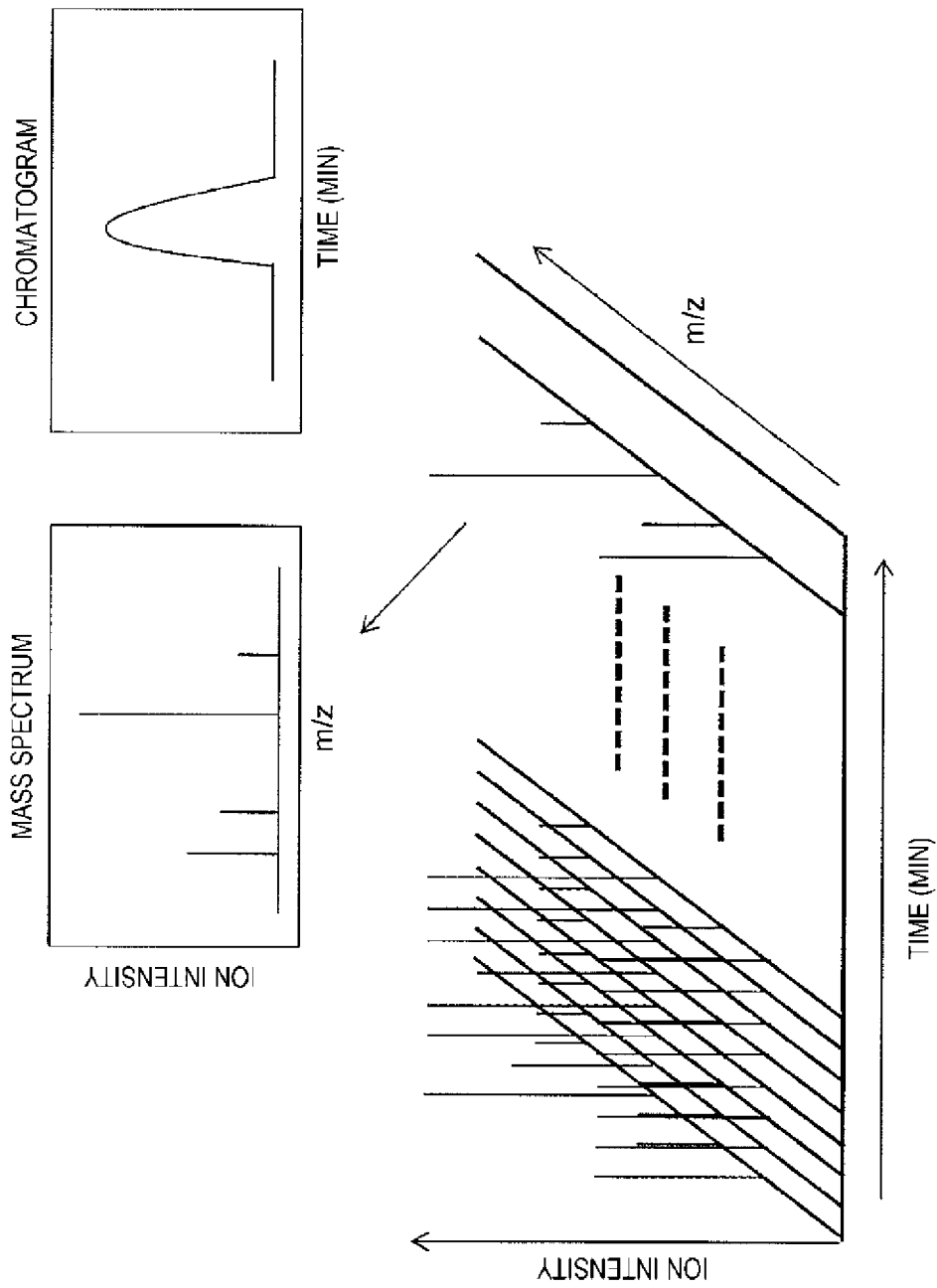
FIG. 3 is a graph showing an example of an LC/MS analysis of colon cancer urine.

A Heat map analysis is to identify a metabolite from the obtained MS spectrum or MS/MS spectrum and to perform comparison of the amounts between samples (cancer patients with respect to healthy individuals). In FIG. 3, an example of the cancer analysis is shown. Based on the results, metabolic pathway coverage and top 30 variable metabolites were picked up.

The results of the Heat map analysis of healthy individuals and cancer patients (breast cancer and colon cancer) are summarized below in Tables 3, 4, and 5.

TABLE 3

Test Design

| Type | Number of specimens |
| --- | --- |
| Healthy individuals | 15 |
| Breast cancer patients | 15 |
| Colon cancer patients | 15 |

TABLE 4

Number of Detected Metabolites

| Number of detected metabolites | |
| --- | --- |
| Total | 1325 |
| Metabolites having unknown structure | 686 |
| Metabolites having known structure | 639 |

TABLE 5

Number of Variable Metabolites (including unknown and known)

| | Breast cancer | | Colon cancer | |
| --- | --- | --- | --- | --- |
| p value | increased | decreased | increased | decreased |
| $P \leq 0.05$ | 208 | 174 | 166 | 512 |
| $0.05 < p < 0.1$ | 66 | 48 | 20 | 61 |

Example 5: Principal Component Analysis

In the principal component analysis, a mutual relationship of explanatory variables (data of metabolites this time) is examined, and a relational expression introducing a new concept objective variable is created. There are a plurality of relational expressions, one is an expression introducing an overall power, and the others are expressions introducing conflicting concept objective variables.

Figure 4:
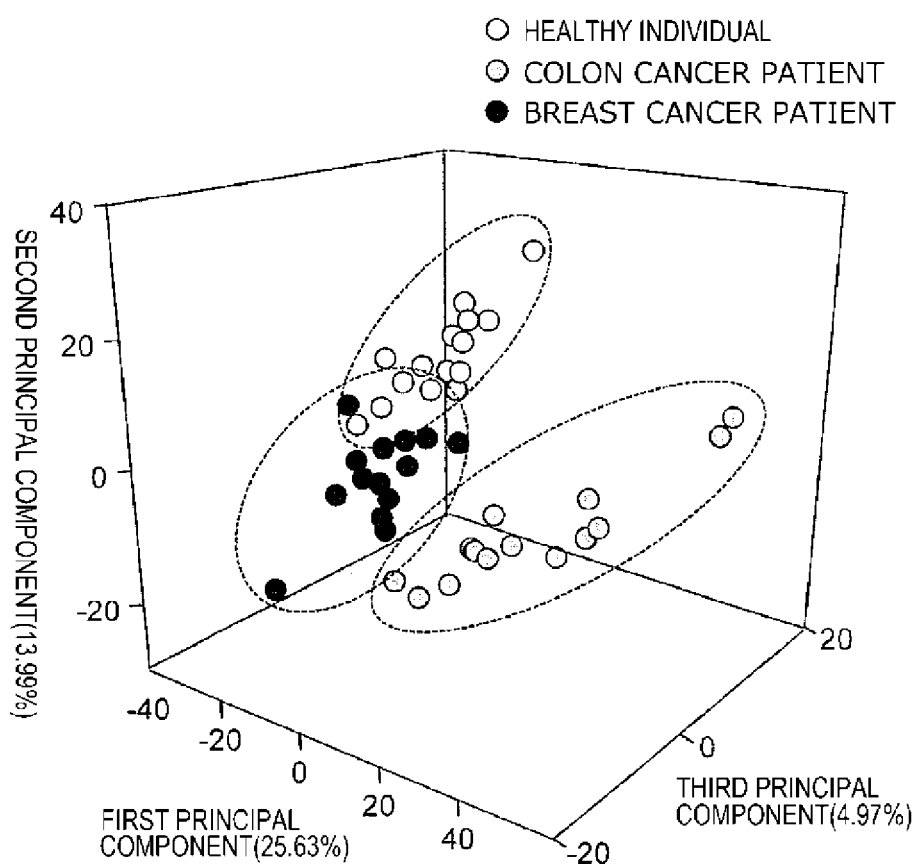
FIG. 4 is a graph showing the results of a principal component analysis which is one type of multivariate analysis of healthy individuals, breast cancer, and colon cancer.

A method used this time is a variance-covariance matrix principal component analysis method. Based on the results, an example of displaying with three objective variables is shown in FIG. 4. The degrees of contribution of the respective objective variables were 25.63% (first component), 13.99% (second component), and 4.97% (third component). The results indicate a possibility of diagnosing a cancer using urine. Heretofore, a cancer test in an in vitro diagnosis mainly using blood has been the mainstream. However, if it is possible to perform a test using urine, there may arise a possibility that a society system in a cancer test itself is changed.

Figure 6B:
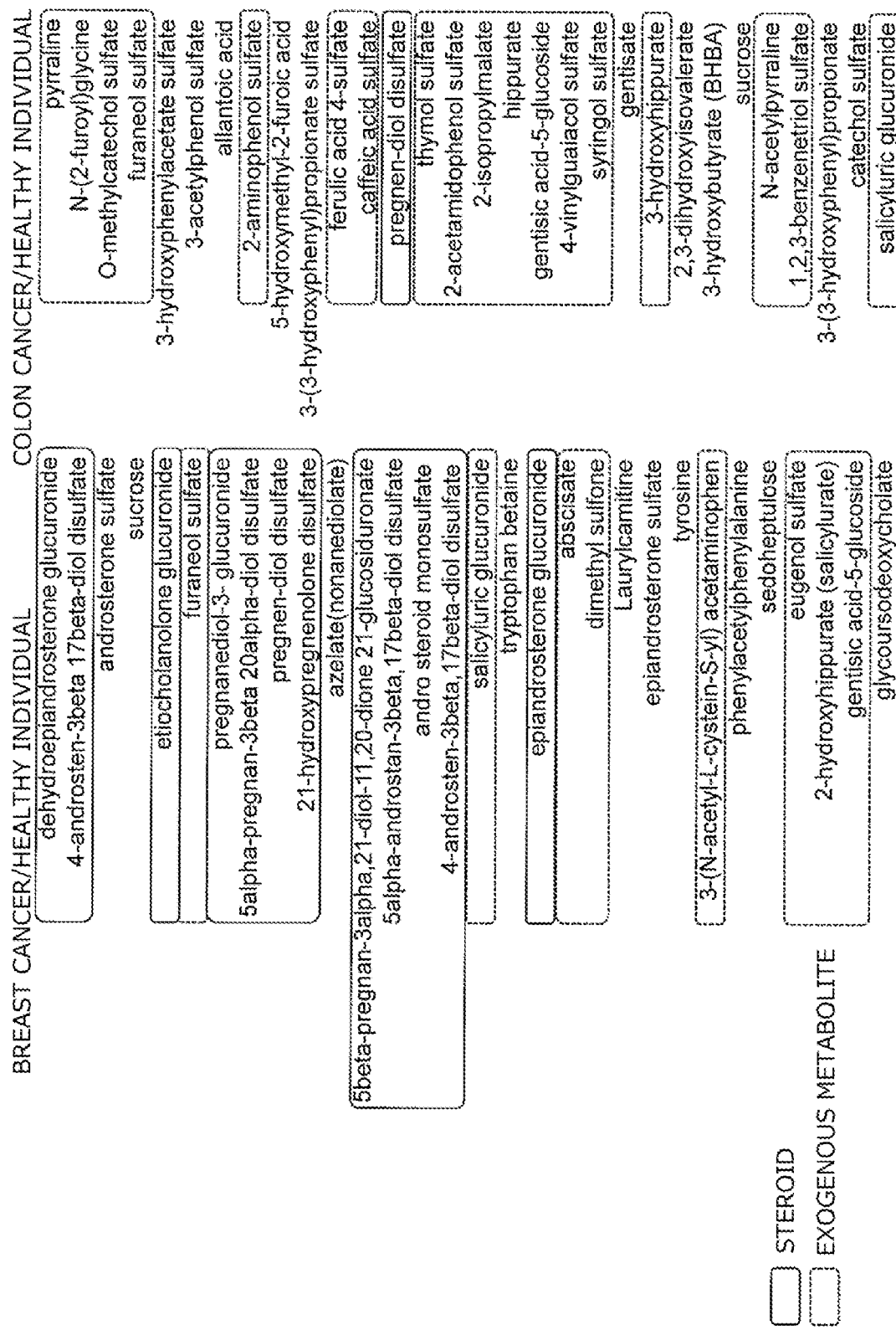
FIG. 6B shows narrowing of biomarker candidate metabolites (only known structures) by a Random Forest analysis.

In order to calculate the importance of the explanatory variable in FIG. 4, a Random Forest analysis method (RF method) was used. When the biomarker candidate metabolites which distinguish various types of cancers from healthy individuals were narrowed down by the RF method, many metabolites with an unknown structure which were not hit by a search in the currently available MS spectrum database were listed up (FIG. 5B, based on the results of the Random Forest analysis in FIG. 5A). On the other hand, when the RF method was performed excluding the metabolites with an unknown structure, steroids as markers which distinguish breast cancer from healthy individuals and exogenous metabolites as biomarkers which distinguish colon cancer from healthy individuals were selected (FIG. 6B, based on the results of the Random Forest analysis in FIG. 6A).

Based on the above analysis results, the biomarker candidates were selected as follows.

TABLE 6

Biomarker candidates obtained by analysis this time

| No. | ID | Mass | Detection platform | Breast/ Healthy | Colon/ Healthy | Filled Value % | | | Comments |
| --- | --- | --- | --- | --- | --- | --- | --- | --- | --- |
| | | | | | | Breast | Colon | Healthy | |
| 1 | X-24589 | 321.1556 | LC/MS neg | 0.07 | 0.07 | 7 | 0 | 100 | Structural isomer of X17697 - both are glucuronide of C8H18O2 |
| 2 | X-17697 | 321.1564 | LC/MS neg | 0.04 | 0.04 | 27 | 20 | 100 | Structural isomer of X24589 - both are glucuronide of C8H18O2 |
| 3 | X-18126 | 134.1175 | LC/MS pos early | 0.06 | 0.1 | 80 | 40 | 100 | Good candidate |
| 4 | X-24546 | 231.0509 | LC/MS neg | 21.65 | 25.29 | 100 | 100 | 80 | Sulfated, but otherwise good candidate |
| 5 | X-16567 | 186.1139 | LC/MS neg | 6.35 | 6.07 | 100 | 100 | 93 | Good candidate |
| 6 | X-23511 | 503.1618 | LC/MS neg | 0.11 | 0.1 | 20 | 7 | 93 | On the larger side at ~503 m/z. Sometimes this makes structure elucidation more difficult |
| 7 | X-11440 | 246.0744 | LC/MS neg | 4.81 | 10.41 | 100 | 100 | 100 | Disulfated steroid |
| 8 | X-17698 | 389.1825 | LC/MS neg | 0.06 | 0.02 | 60 | 27 | 87 | Glucuronide of C12H22O3 |
| 9 | X-12726 | 233.0129 | LC/MS neg | 0.34 | 0.12 | 100 | 100 | 100 | Glucuronide of C14H26O4 |
| 10 | X-12831 | 433.2088 | LC/MS neg | 0.23 | 0.05 | 100 | 87 | 100 | We think this is something like 3,4-dihydroxyphenylethyl sulfate. |
| 11 | X-12636 | 257.1511 | LC/MS neg | 4.98 | 6.84 | 100 | 100 | 100 | We think this may be methylhexanoyl glutamine. |
| 12 | X-24502 | 208.0966 | LC/MS pos early | 0.31 | 0.11 | 100 | 93 | 100 | We think this may be phenylacetylalanine (not N-acetylphenylalanine, they do not coelute). |
| 13 | X-23787 | 383.1531 | LC/MS neg | 11.13 | 8.78 | 100 | 87 | 47 | Likely isomer of hydroxy DHEA-sulfate |
| 14 | X-21470 | 232.0595 | LC/MS neg | 7.6 | 14.3 | 100 | 100 | 73 | Sulfated |
| 15 | X-24495 | 479.2277 | LC/MS neg | 7.21 | 4.71 | 100 | 87 | 67 | Glucuronides of C19H28O3 |
| 16 | X-15497 | 236.093 | LC/MS neg | 0.24 | 0.1 | 100 | 80 | 100 | C12H15NO4 |
| 17 | X-24473 | 146.0811 | LC/MS pos early | 0.42 | 0.07 | 93 | 40 | 100 | C6H11NO3 |
| 18 | X-17324 | 342.2269 | LC/MS pos early | 4.99 | 5.76 | 100 | 100 | 93 | Several potential formulas |
| 19 | X-22379 | 465.2504 | LC/MS neg | 6.26 | 4.18 | 100 | 100 | 87 | We think this is androsterone glucuronide |

Example 6: Urinary Marker Candidates

As the urine marker candidates, with respect to X-18126, X-24546, X-16567, X-11440, X-12831, X-12636, X-24502, and X-23787 shown in Table 6, an analysis was further performed.

Figure 8:
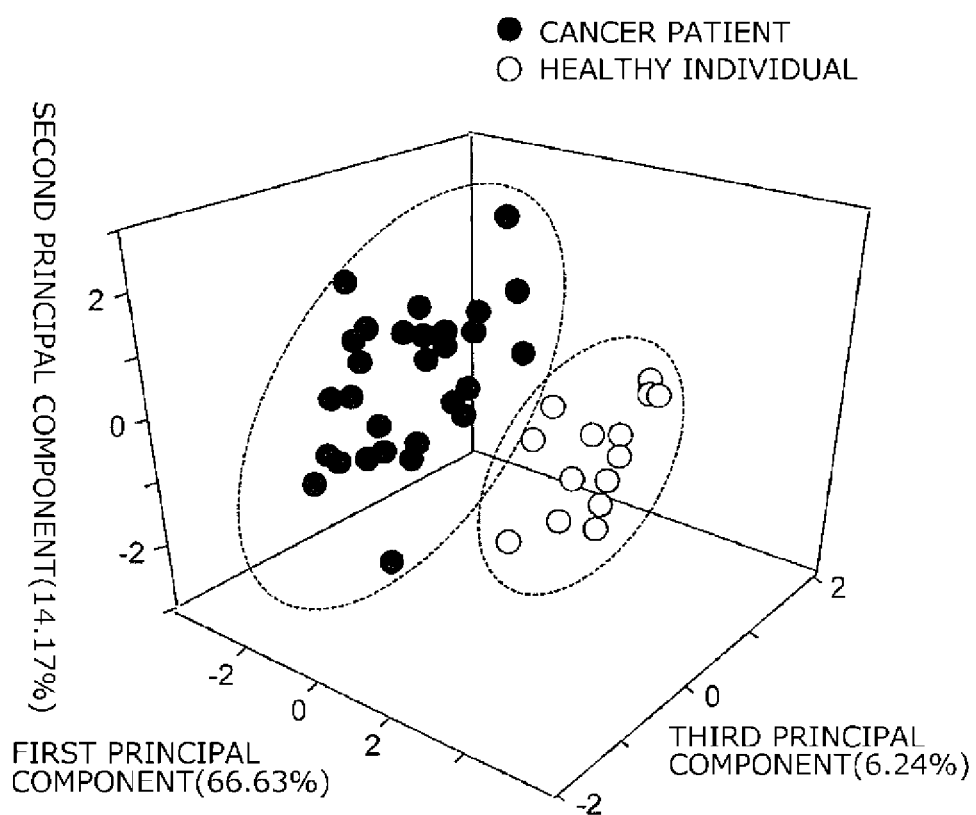
FIG. 8 is a graph showing the effectiveness of urinary marker candidates (8 types) by a principal component analysis which is one type of multivariate analysis.

The results are shown in the following Table 7 and FIGS. 7 and 8.

TABLE 7

Effectiveness of Urinary Marker Candidates by Random Forest Analysis
Prediction accuracy: 97.78%

| Random forest | | Prediction group | | Error |
|---|---|---|---|---|
| | | Cancer | Healthy | |
| Actual group | Cancer | 30 | 0 | 0.0000 |
| | Healthy | 1 | 14 | 0.0667 |

From the above analysis, the effectiveness of the urinary metabolites X-18126, X-24546, X-16567, X-11440, X-12831, X-12636, X-24502, and X-23787 as a urinary marker was demonstrated.

Example 7: Analysis of Combination of Urinary Marker Candidates

In order to examine a combination of urinary marker candidates, with respect to the urine specimens of cancer patients (N=30) and the healthy individuals (N=15), a principal component analysis using the following combinations of the metabolites was performed:

(1) a principal component analysis in the case of using only 2 types of urinary metabolites X-18126 and X-16567;

(2) a principal component analysis in the case of using only 3 types of urinary metabolites X-18126, X-16567, and X-24546;

(3) a principal component analysis in the case of using 8 types of urinary metabolites X-18126, X-16567, X-24546, X-11440, X-12831, X-12636, X-24502, and X-23787;

(4) a principal component analysis in the case of using 19 types of urinary metabolites X-24589, X-17697, X-18126, X-24546, X-16567, X-23511, X-11440, X-17698, X-12726, X-12831, X-12636, X-24502, X-23787, X-21470, X-24495, X-15497, X-24473, X-17324, and X-22379;

(5) a principal component analysis in the case of using 30 types of urinary metabolites X-24589, X-17697, X-18126, pyrraline, X-24584, dehydroepiandrosterone glucuronide, X-24577, X-12329, X-12267, X-22850, 2-aminophenol sulfate, X-24760, X-12731, 3-(3-hydroxyphenyl)propionate sulfate, furaneol sulfate, X-12007, 2-acetamidephenol sulfate, 3-acetylphenol sulfate, X-23511, X-21807, N-(2-furoyl)glycine, X-24497, X-16567, X-12818, X-24528, X-17707, X-21295, X-24579, X-17324, and X-24495; and (6) a principal component analysis in the case of using all the observed 1325 types of urinary metabolites.

Figure 9A:
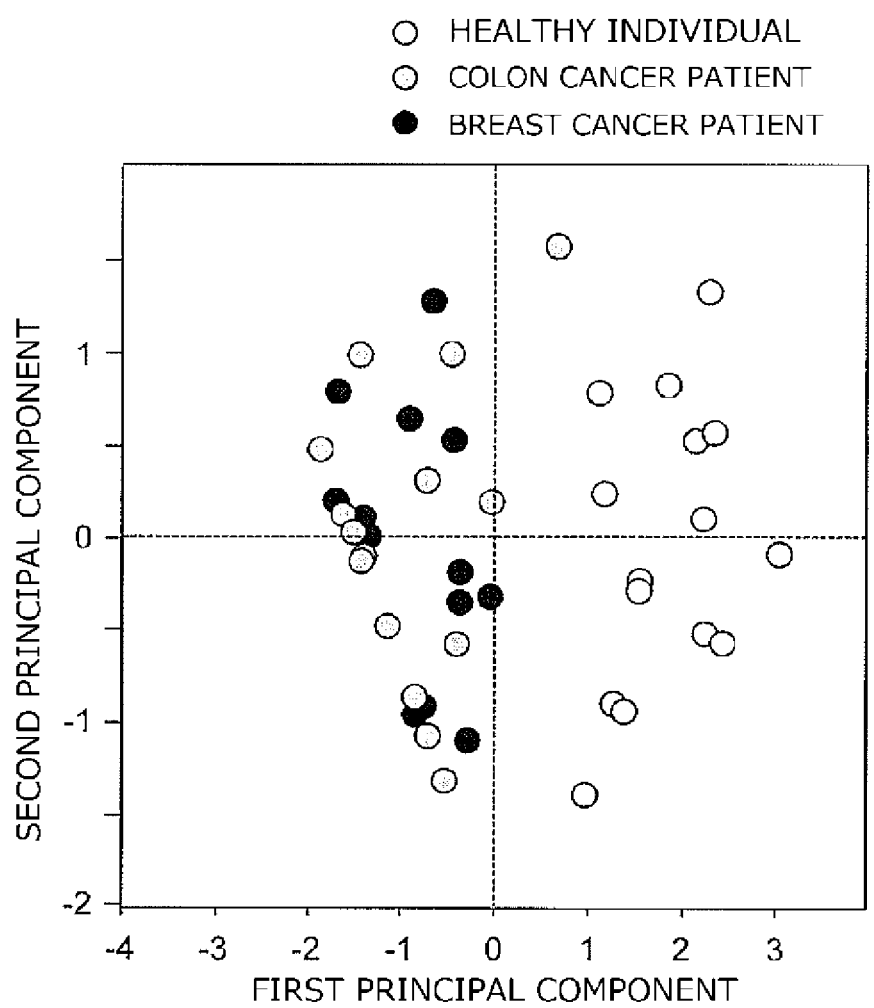
FIG. 9A is a graph showing the effectiveness of urinary markers (2 types) by a principal component analysis which is one type of multivariate analysis.
Figure 9C:
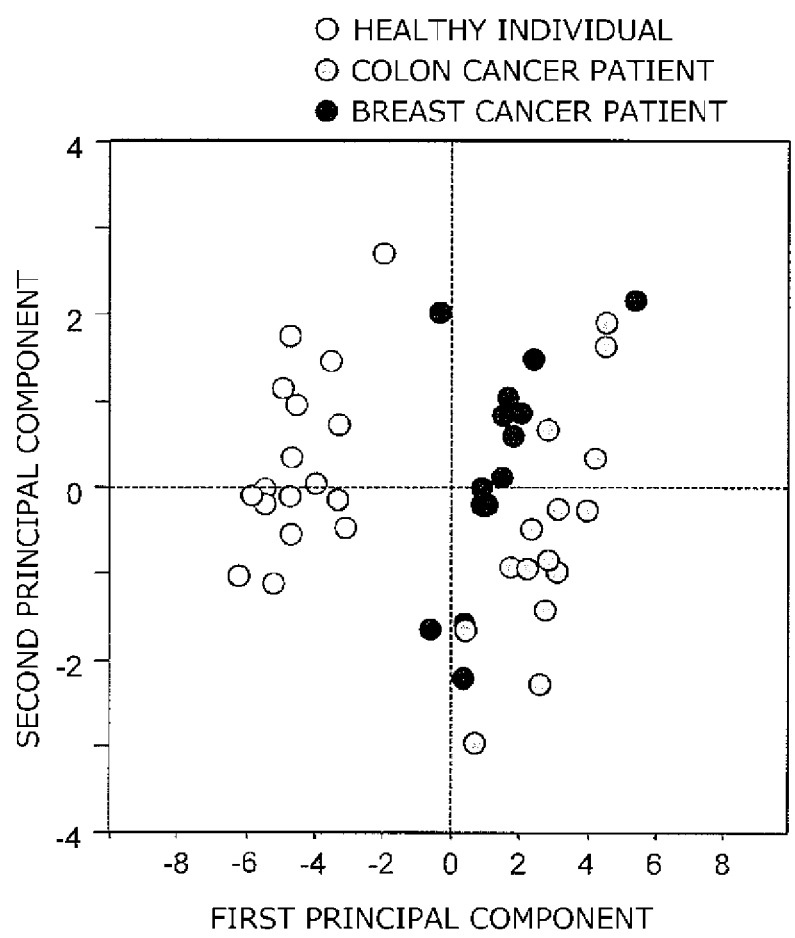
FIG. 9C is a graph showing the effectiveness of urinary markers (8 types) by a principal component analysis which is one type of multivariate analysis.
Figure 9D:
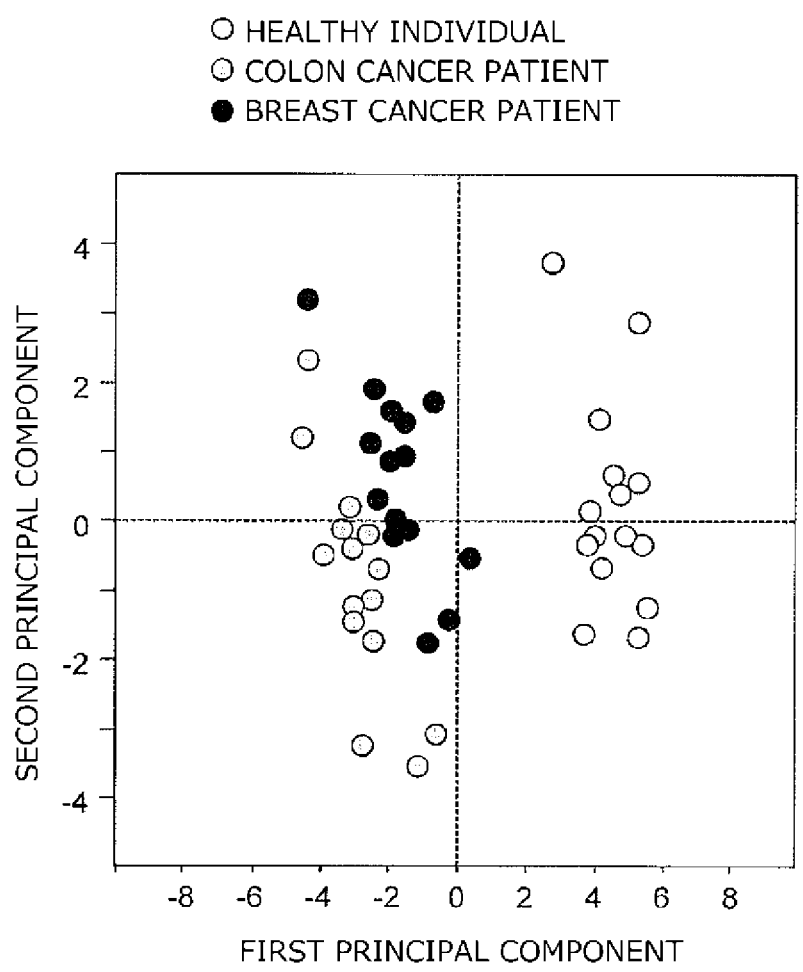
FIG. 9D is a graph showing the effectiveness of urinary markers (19 types) by a principal component analysis which is one type of multivariate analysis.
Figure 9E:
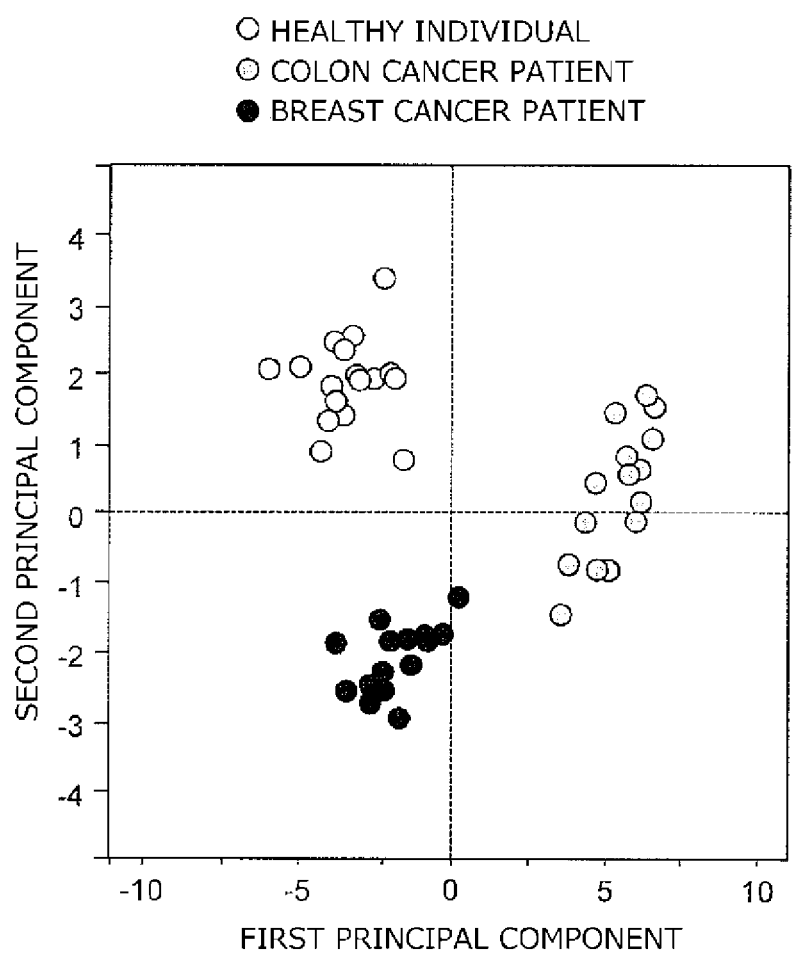
FIG. 9E is a graph showing the effectiveness of urinary markers (30 types) by a principal component analysis which is one type of multivariate analysis.
Figure 9F:
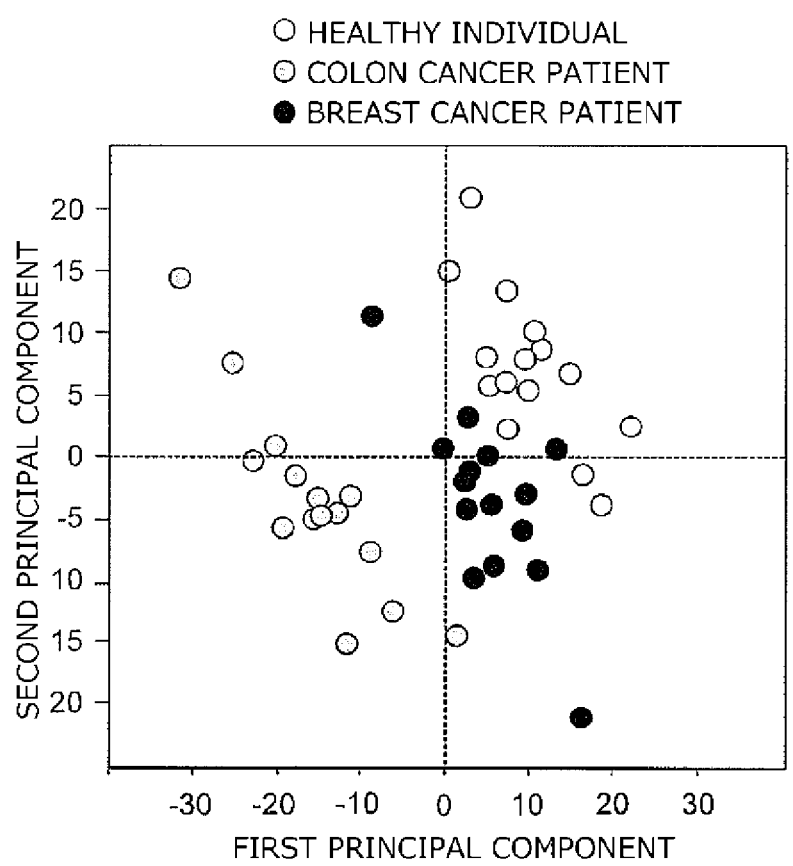
FIG. 9F is a graph showing the effectiveness of urinary markers (1325 types) by a principal component analysis which is one type of multivariate analysis.
Figure 11:
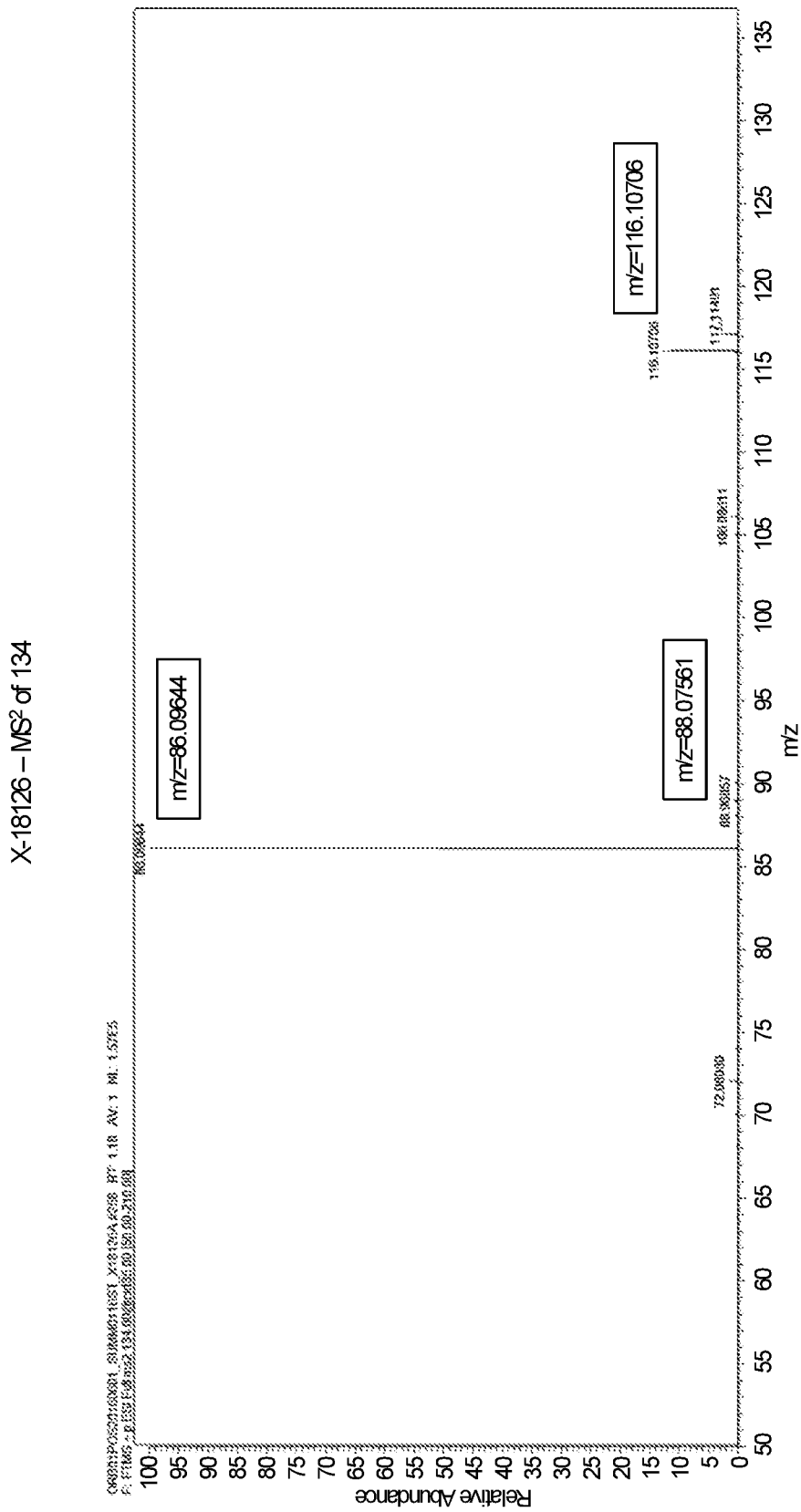
FIG. 11 shows MS/MS data for the metabolite X-18126.

The results of the principal component analyses (1) to (6) are shown in FIG. 9A (2 types of metabolites), FIG. 9B (3 types of metabolites), FIG. 9C (8 types of metabolites), FIG. 9D (19 types of metabolites), FIG. 9E (30 types of metabolites), and FIG. 9F (1325 types of metabolites), respectively.

As shown in FIGS. 9A and 9B, it is found that when using a combination of biomarkers (a combination of X-18126 and X-16567 or a combination of X-18126, X-16567, and X-24546) which are considered to be particularly important, healthy individuals and cancer patients (colon cancer patients and breast cancer patients) can be distinguished, and these results indicate that X-18126, X-16567, and X-24546 are potent biomarkers. By examining which zone the specimen of a test subject belongs to using the 2 types of metabolites or the 3 types of metabolites as a primary test, it is possible to determine whether or not the subject is suspected of having a cancer.

On the other hand, as shown in FIGS. 9C and 9D, when increasing the number of biomarkers to be used in the principal component analysis to 8 types to 19 types, the ability to distinguish healthy individuals from cancer patients (colon cancer patients and breast cancer patients) is improved. Further, as shown in FIG. 9E, it is found that when increasing the number of biomarkers to 30 types, it is possible not only to distinguish healthy individuals from cancer patients, but also to distinguish breast cancer patients from colon cancer patients. Incidentally, as shown in FIG. 9F, when using all the measured metabolites in the principal component analysis, although distinction is possible, the degree of distinction is slightly decreased.

By examining which zone the specimen of a test subject falls under using 30 types of metabolites in the above (5) or 20 to 29 types of metabolites including X-18126 and X-16567 among the 30 types of metabolites as a primary test or as a secondary test after the primary test or further as a third test after the secondary test, it is found that whether or not the subject is suspected of having a cancer. In addition, the type of the cancer can also be predicted.

The above results indicate that by controlling the number of biomarkers, a multistage test of a test for all cancer types (various cancer types are tested at one time) and a test for each cancer type (a specific cancer type is tested) can be performed.

Example 8: Analysis of Urinary Marker Candidates

With respect to X-18126, X-24546, X-16567, X-11440, X-12831, X-12636, X-24502, and X-23787 shown in Table 6 as urinary marker candidates, the LC/MS data described in Example 3 were analyzed. Further, an $MS^n$ analysis was also performed.

Figure 12:
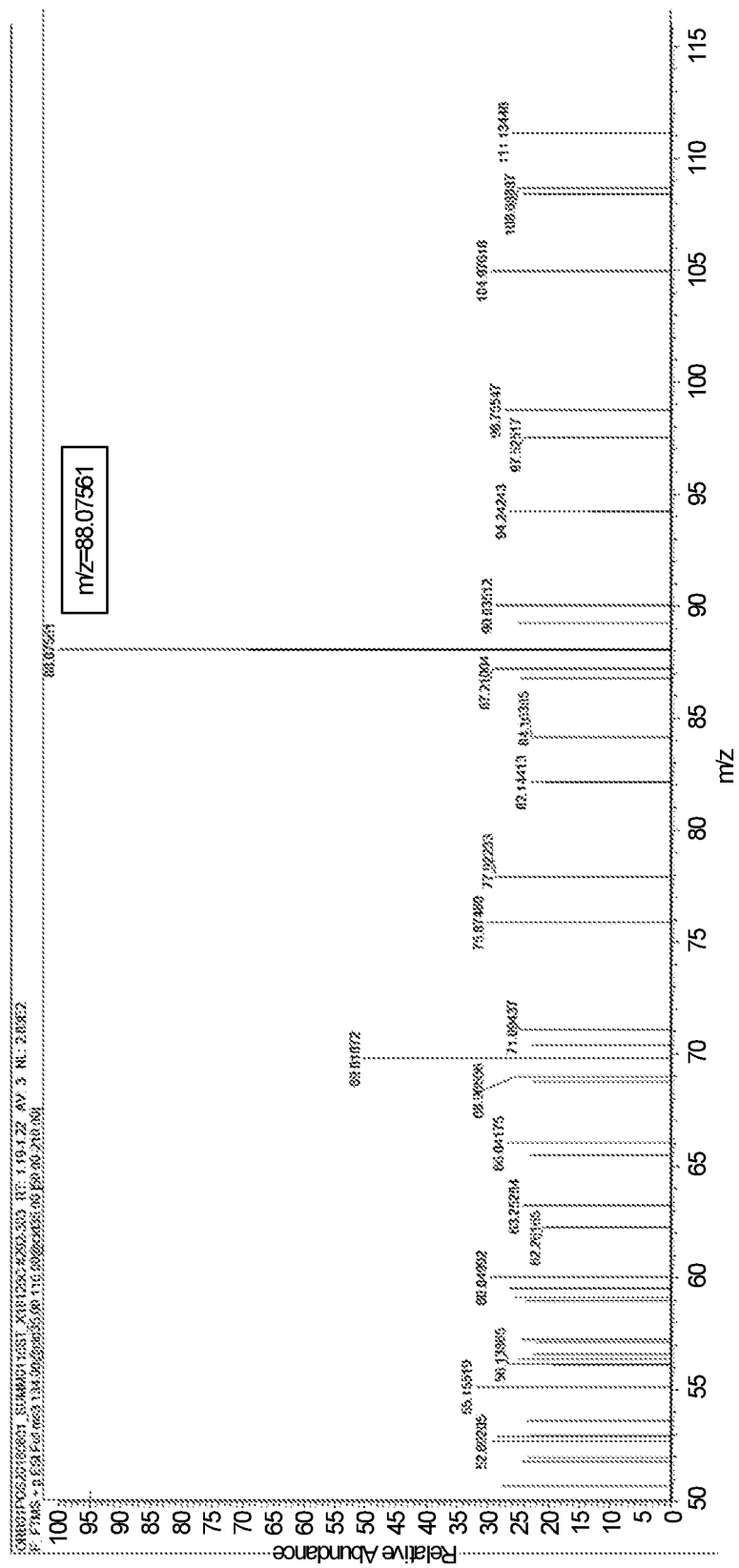
FIG. 12 shows MS/MS/MS data for the metabolite X-18126.
Figure 13:
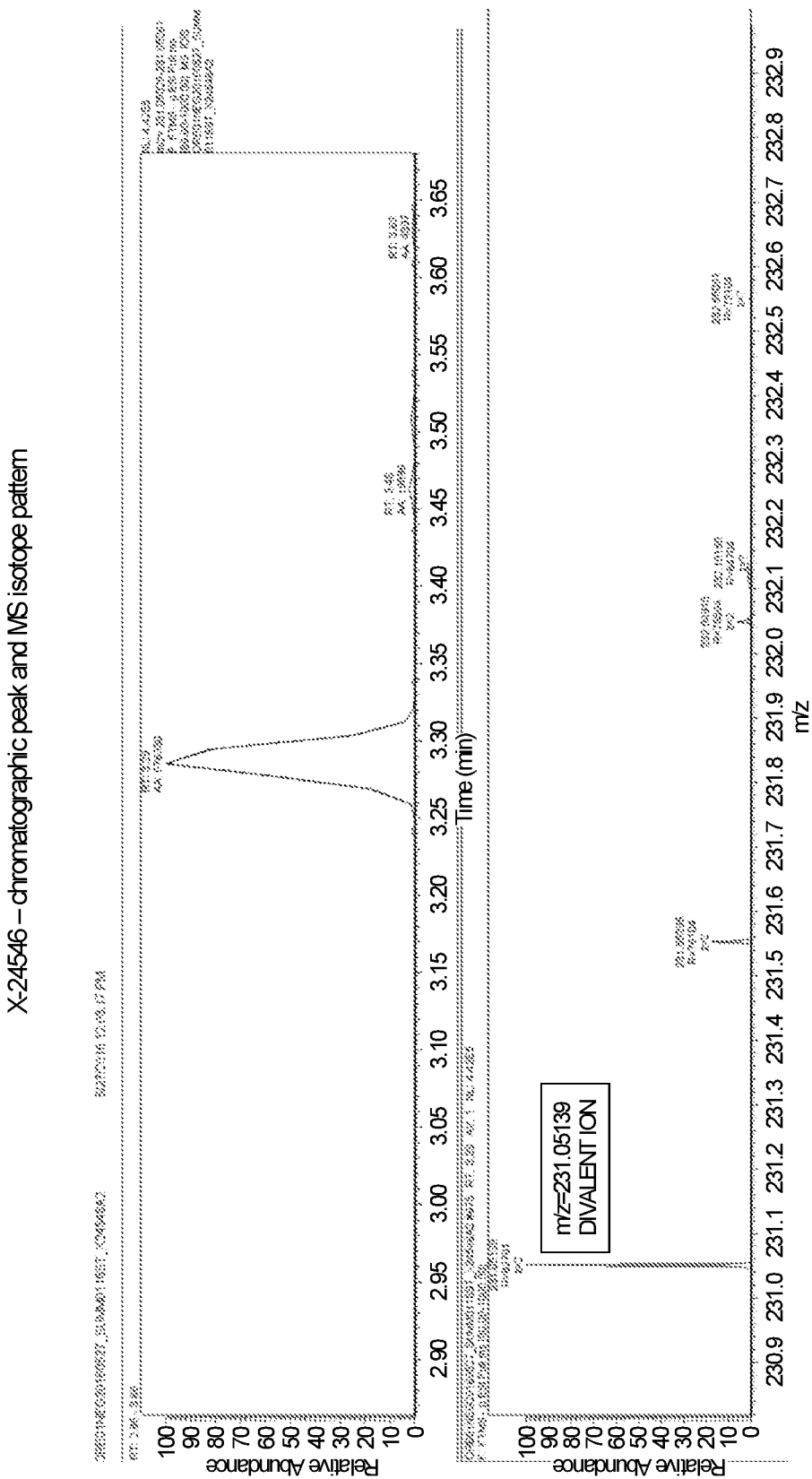
FIG. 13 shows LC/MS data for the metabolite X-24546.
Figure 14:
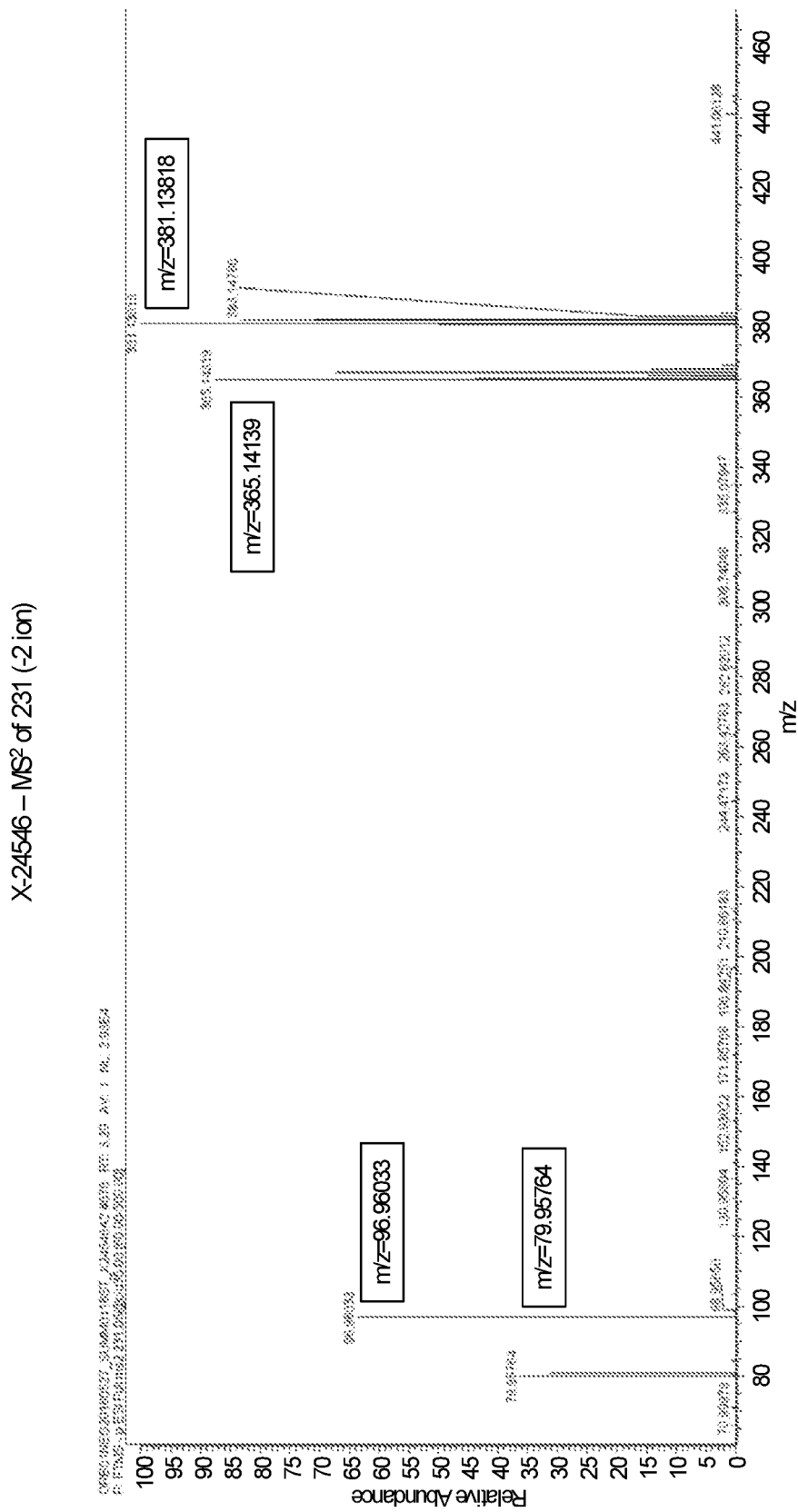
FIG. 14 shows MS/MS data for the metabolite X-24546.
Figure 15:
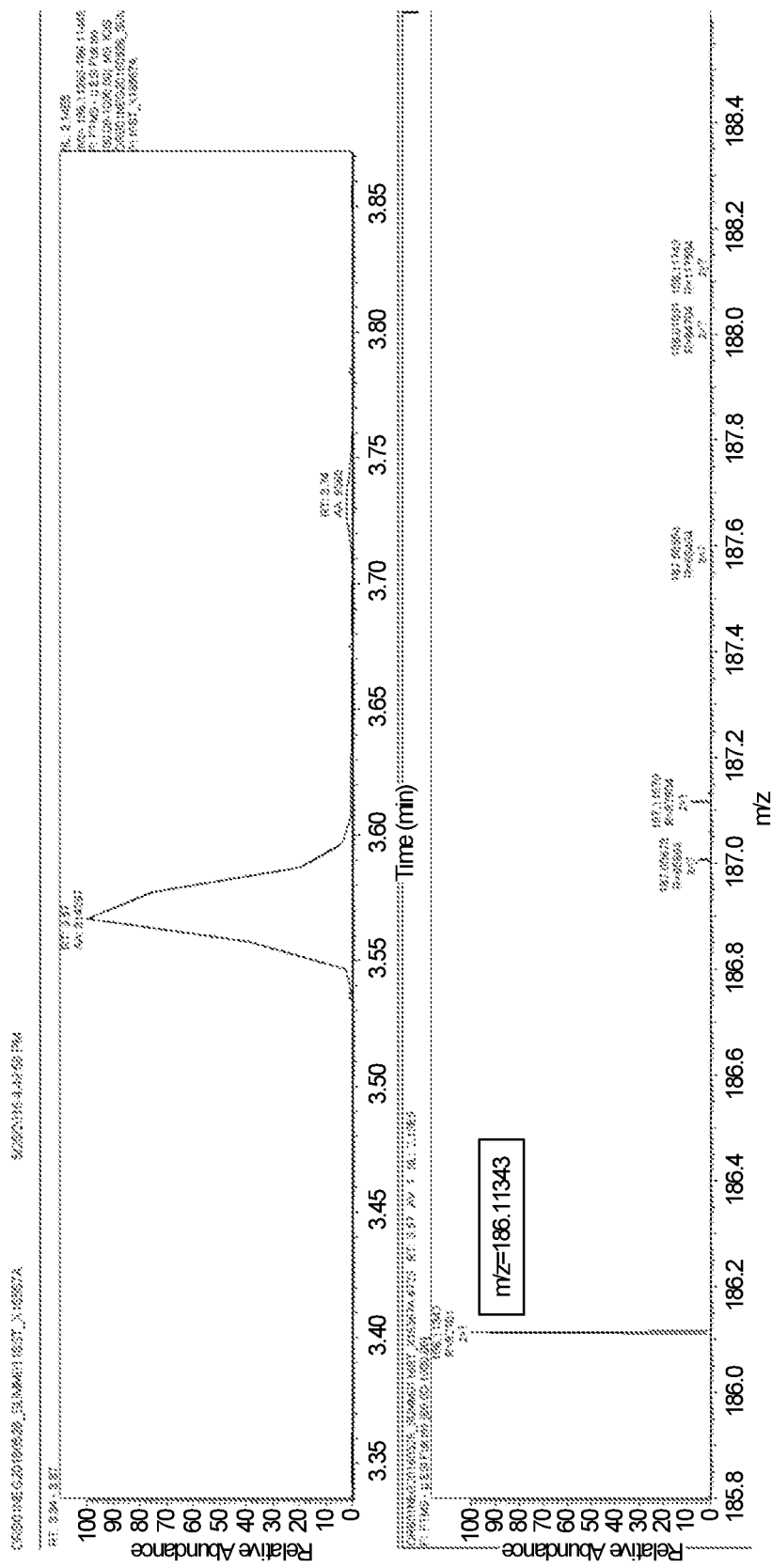
FIG. 15 shows LC/MS data for the metabolite X-16567.
Figures 1, 16:
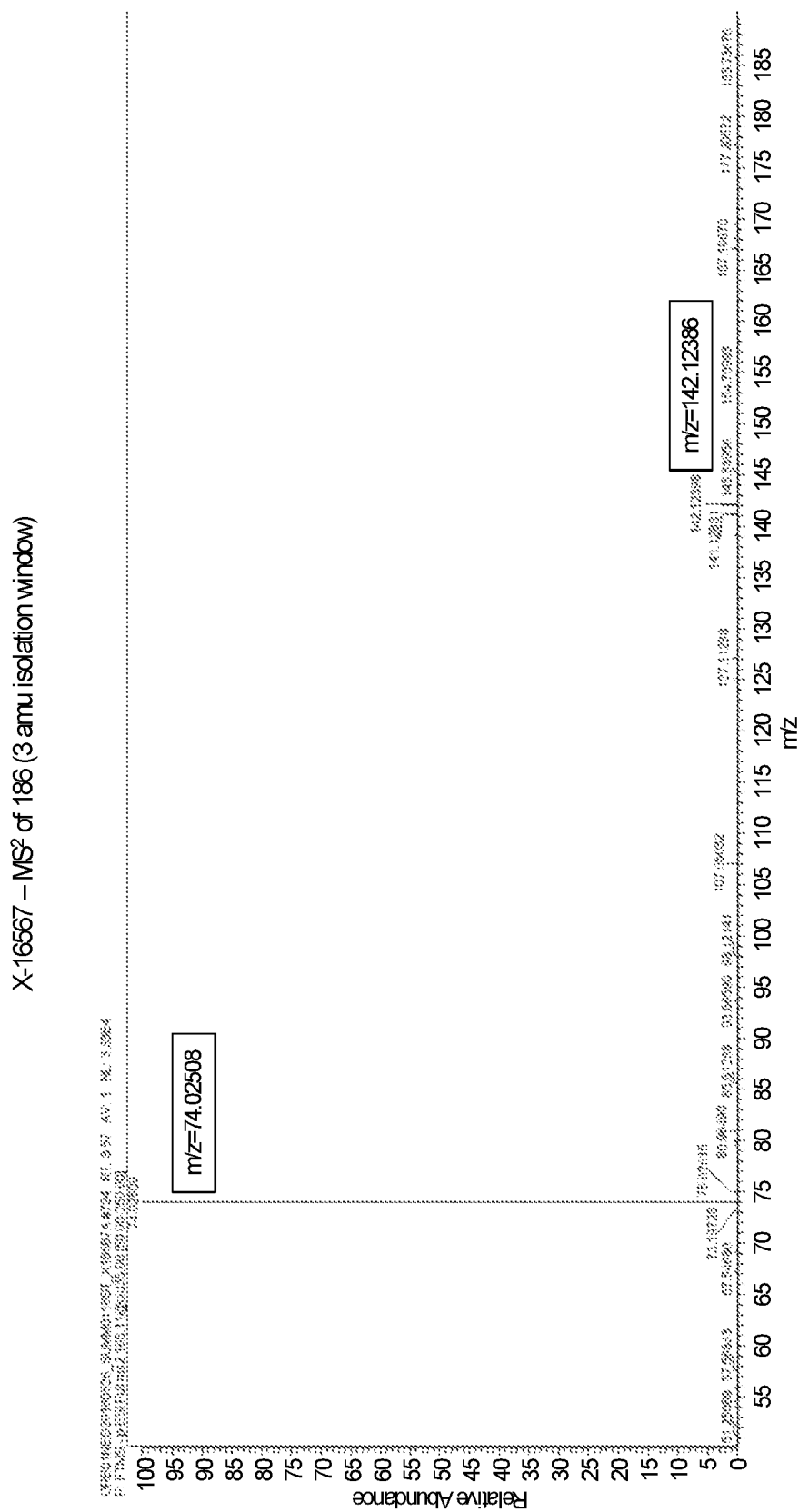
Figures 2, 16:
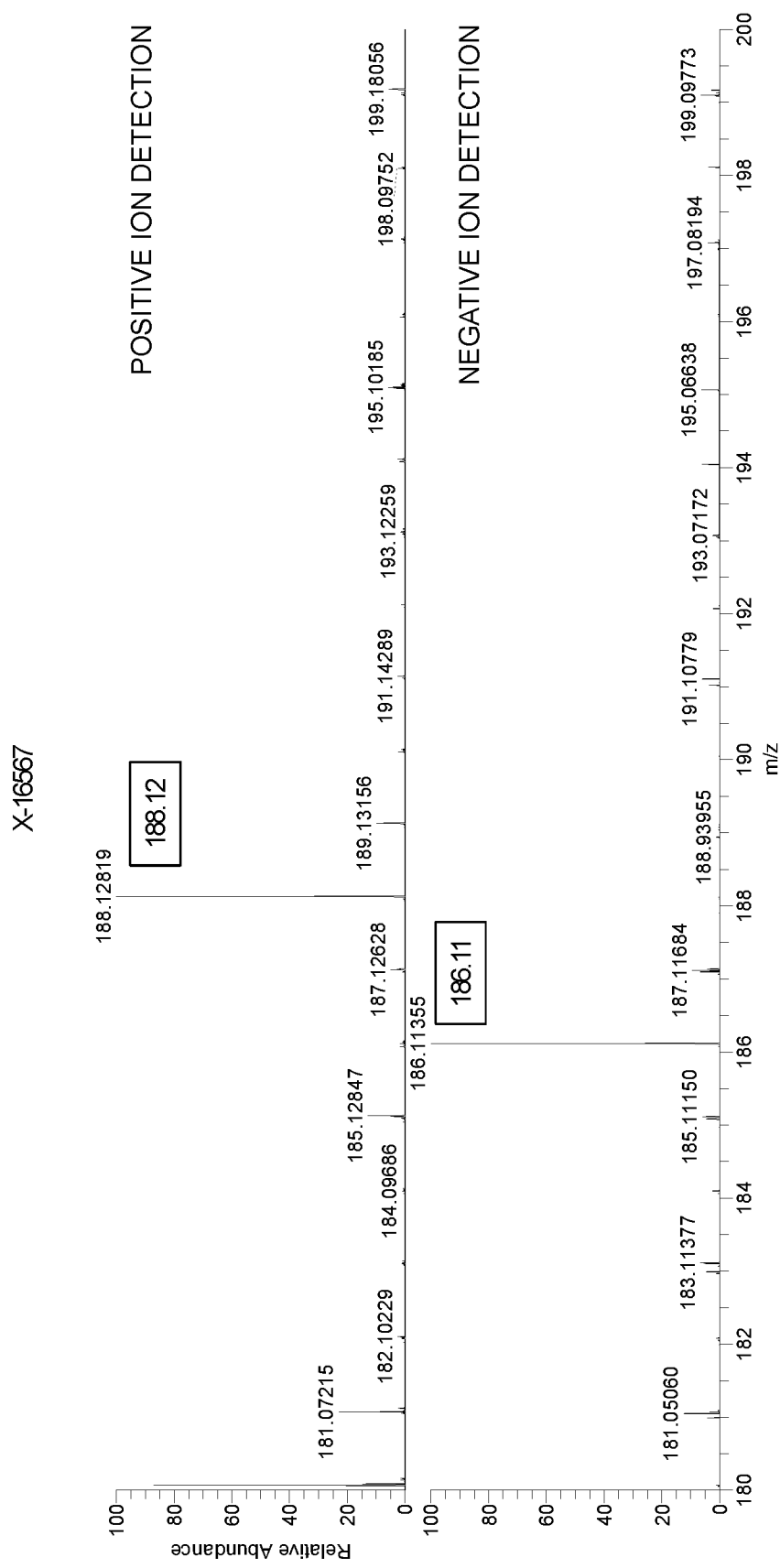
Figure 17:
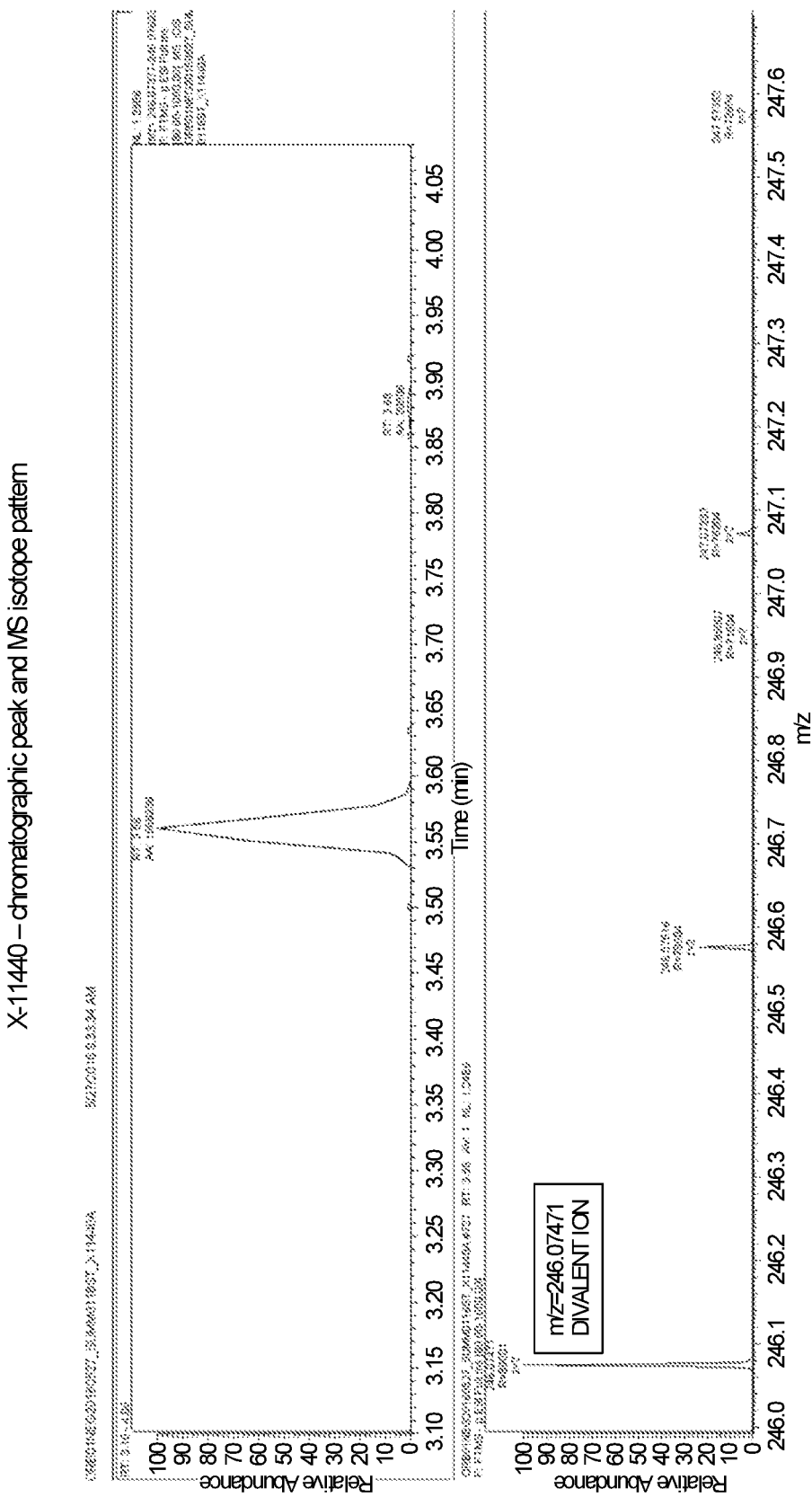
FIG. 17 shows LC/MS data for the metabolite X-11440.
Figures 1, 18:
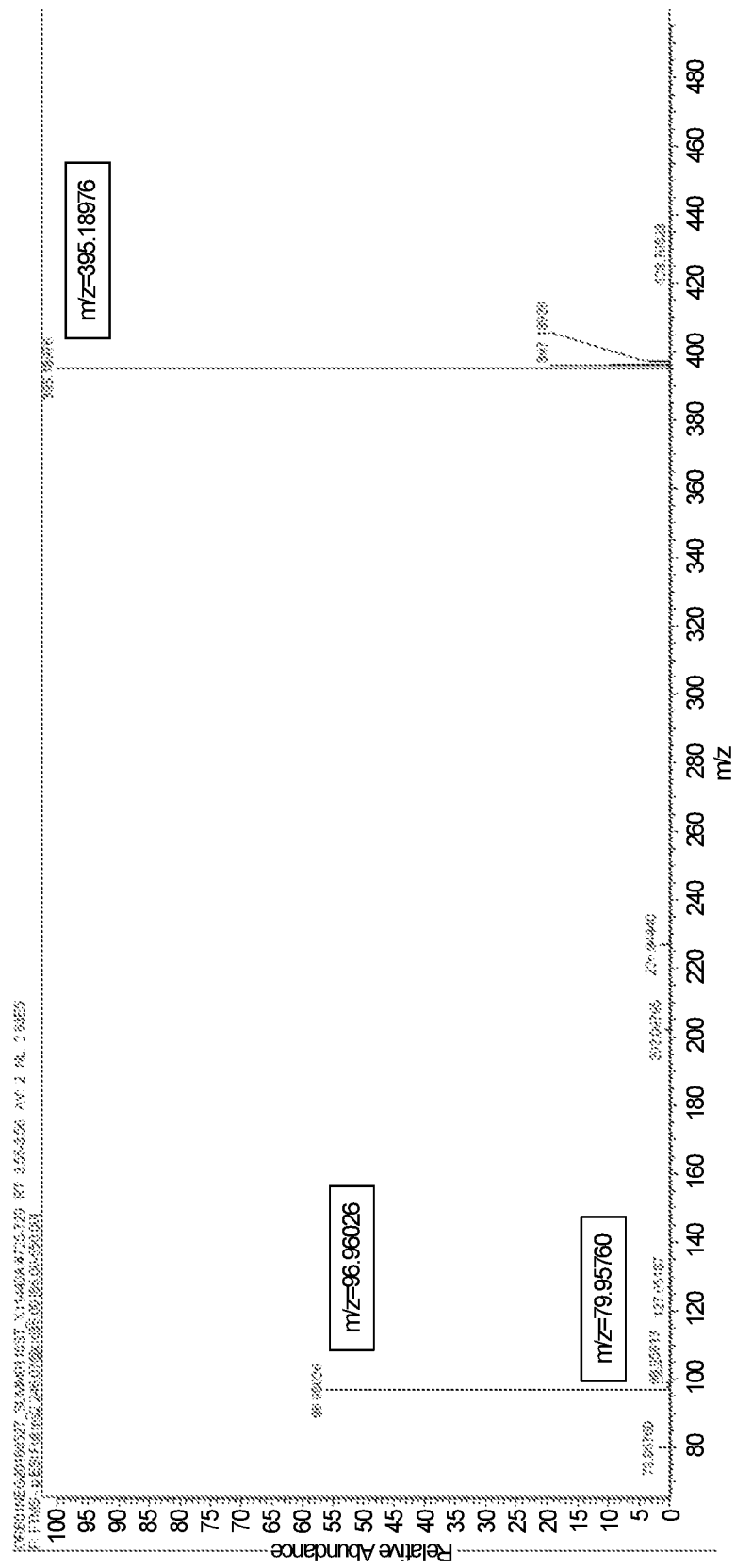
Figures 2, 18:
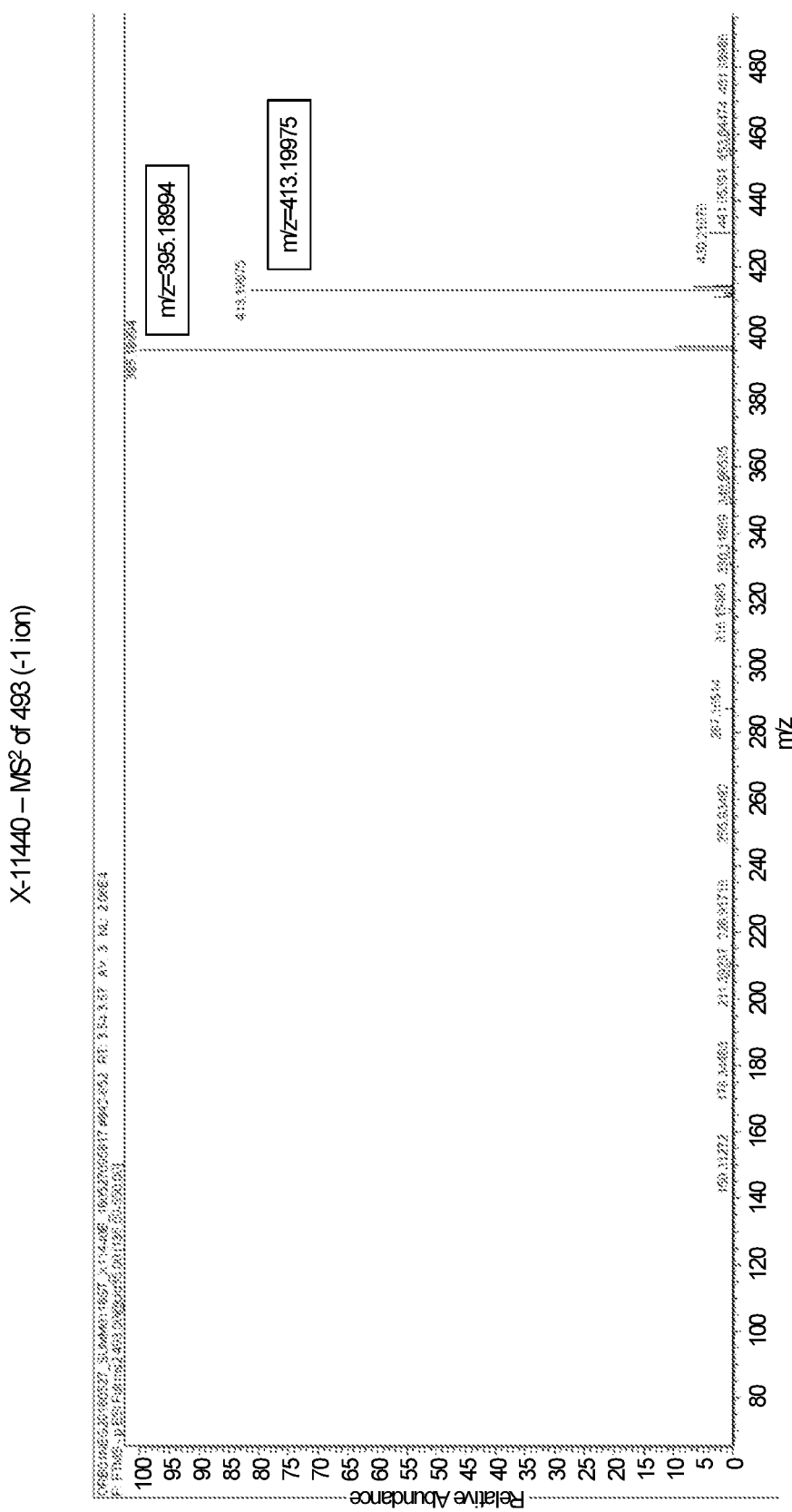
Figure 19:
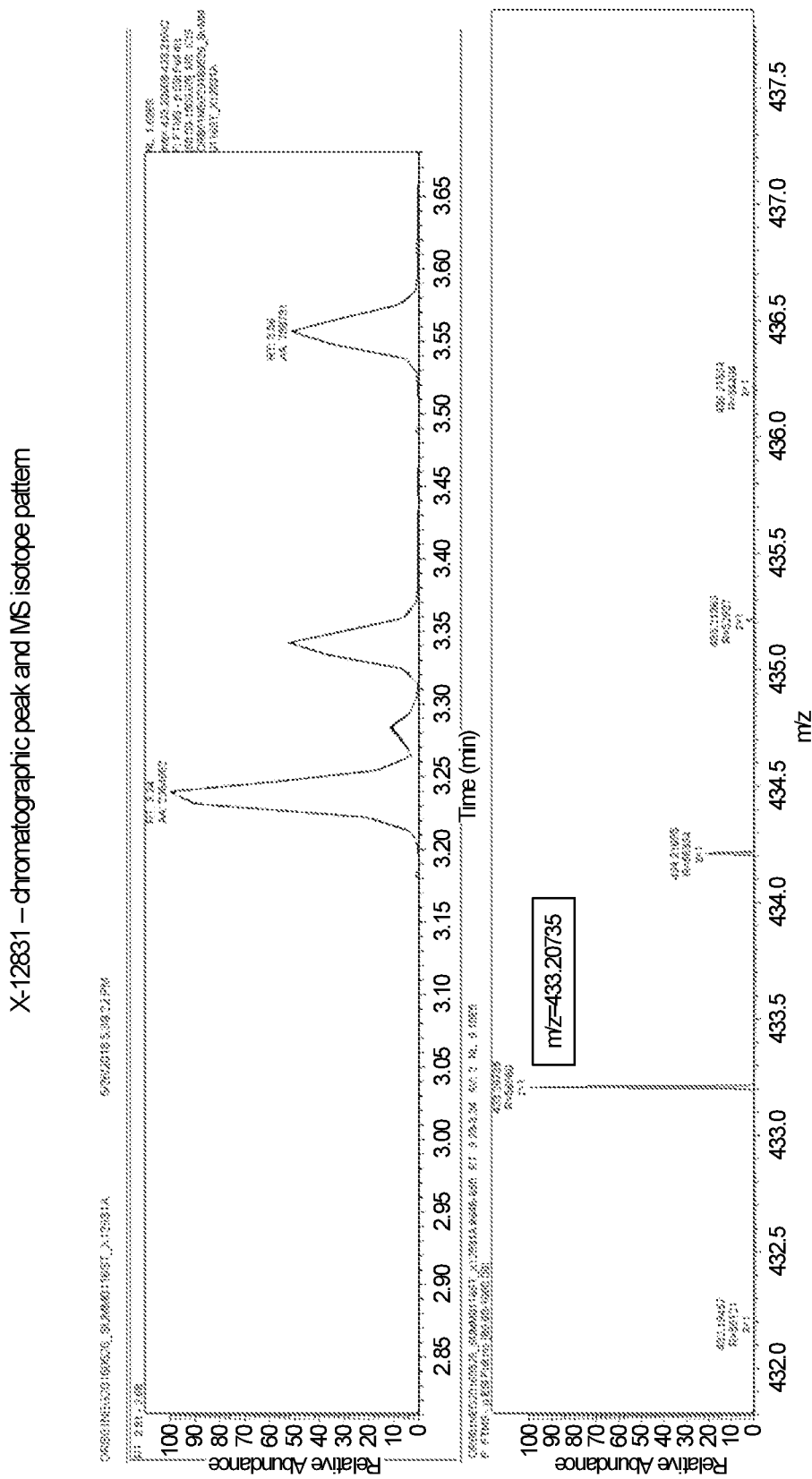
FIG. 19 shows LC/MS data for the metabolite X-12831.
Figures 1, 20:
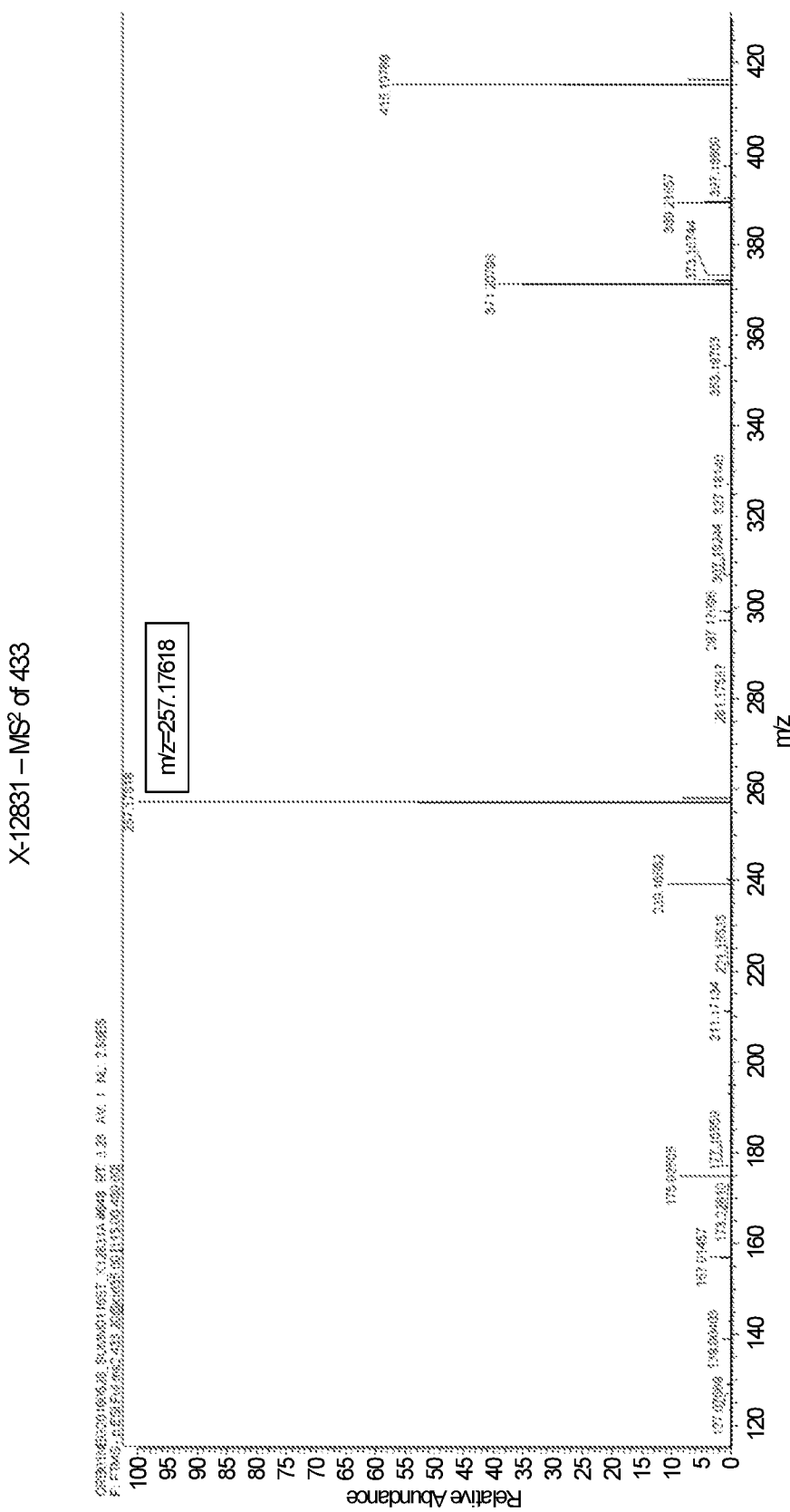
Figures 2, 20:
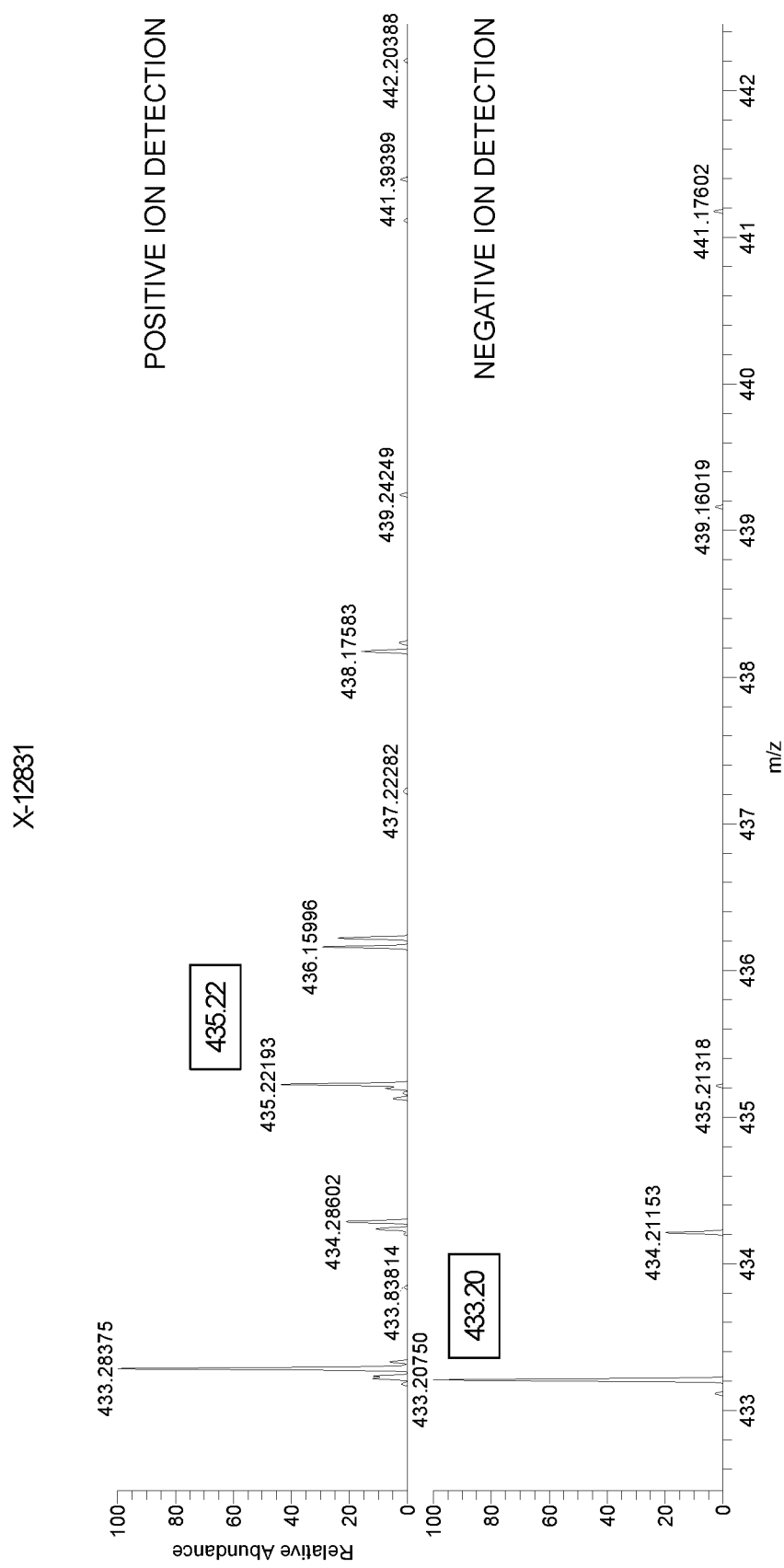
Figure 21:
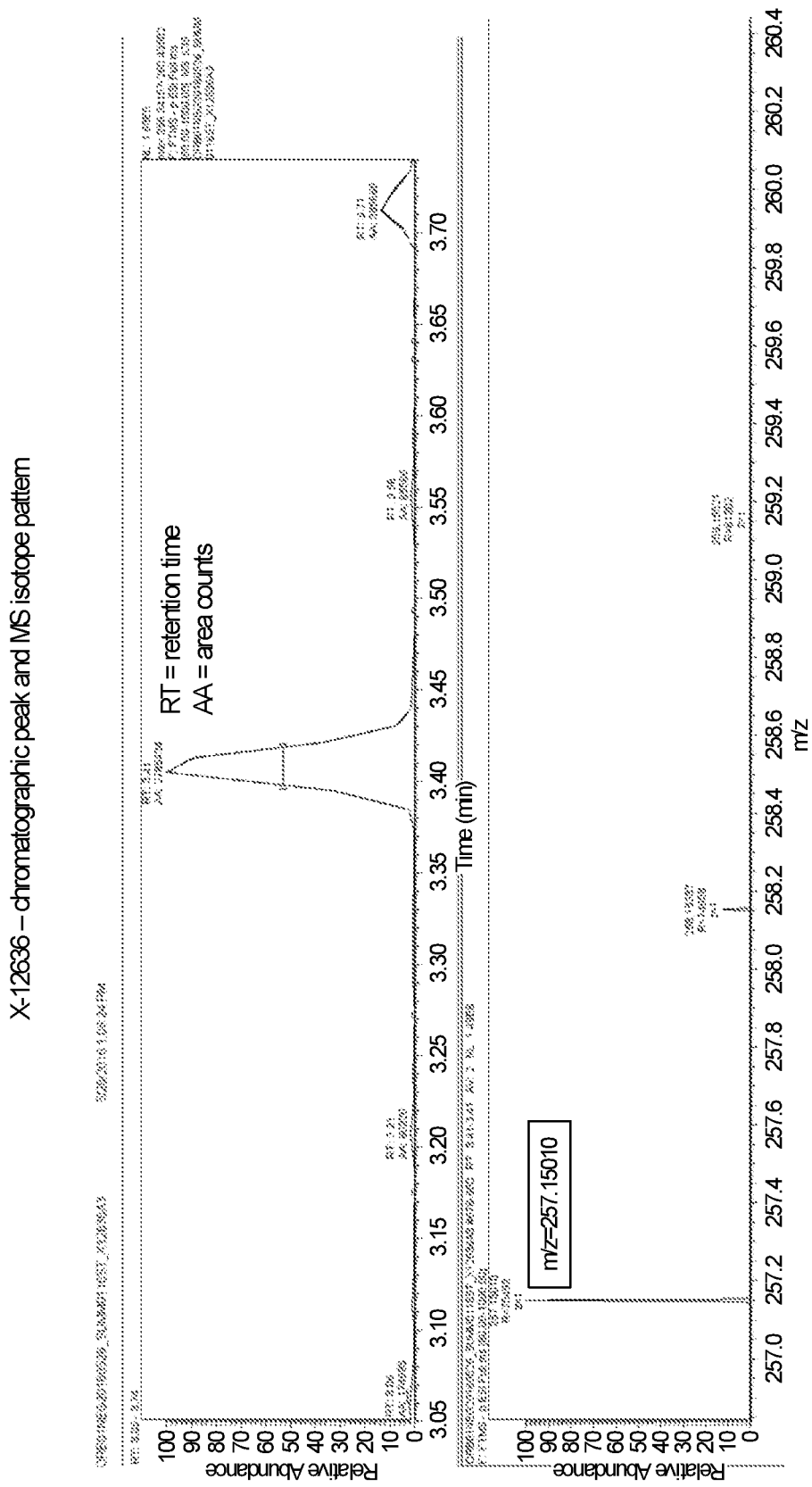
FIG. 21 shows LC/MS data for the metabolite X-12636.
Figures 1, 22:
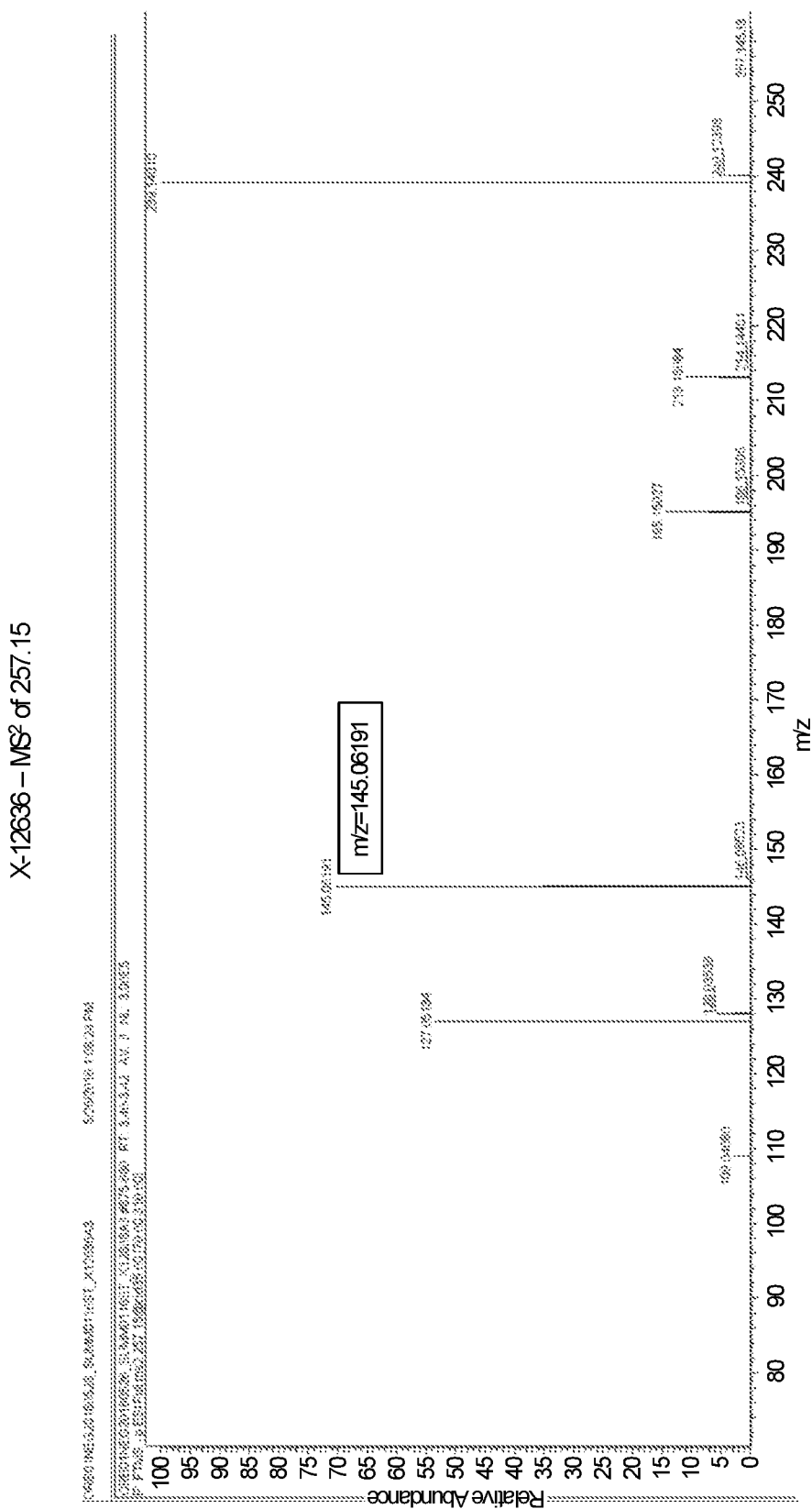
Figures 2, 22:
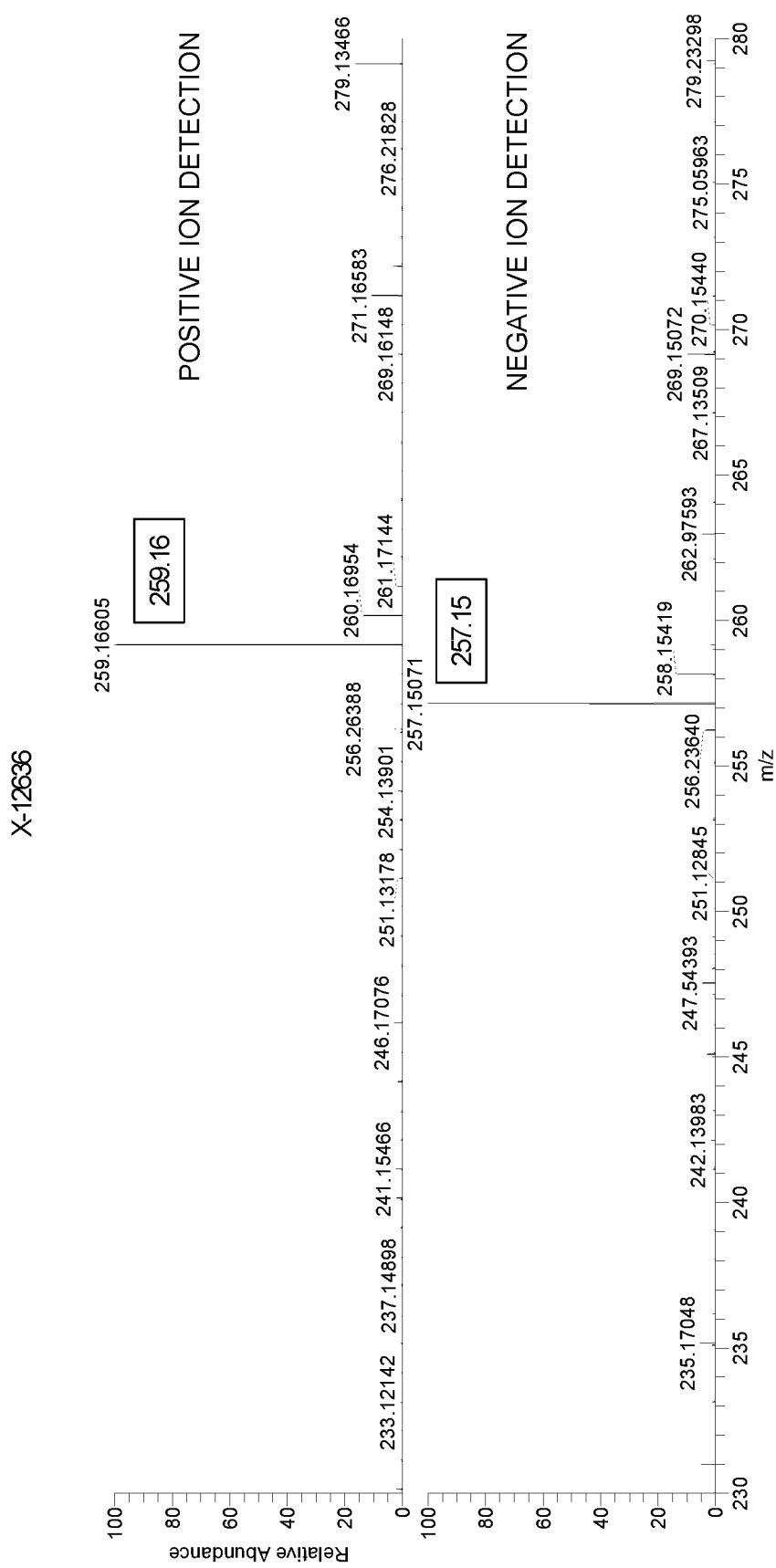
Figure 23:
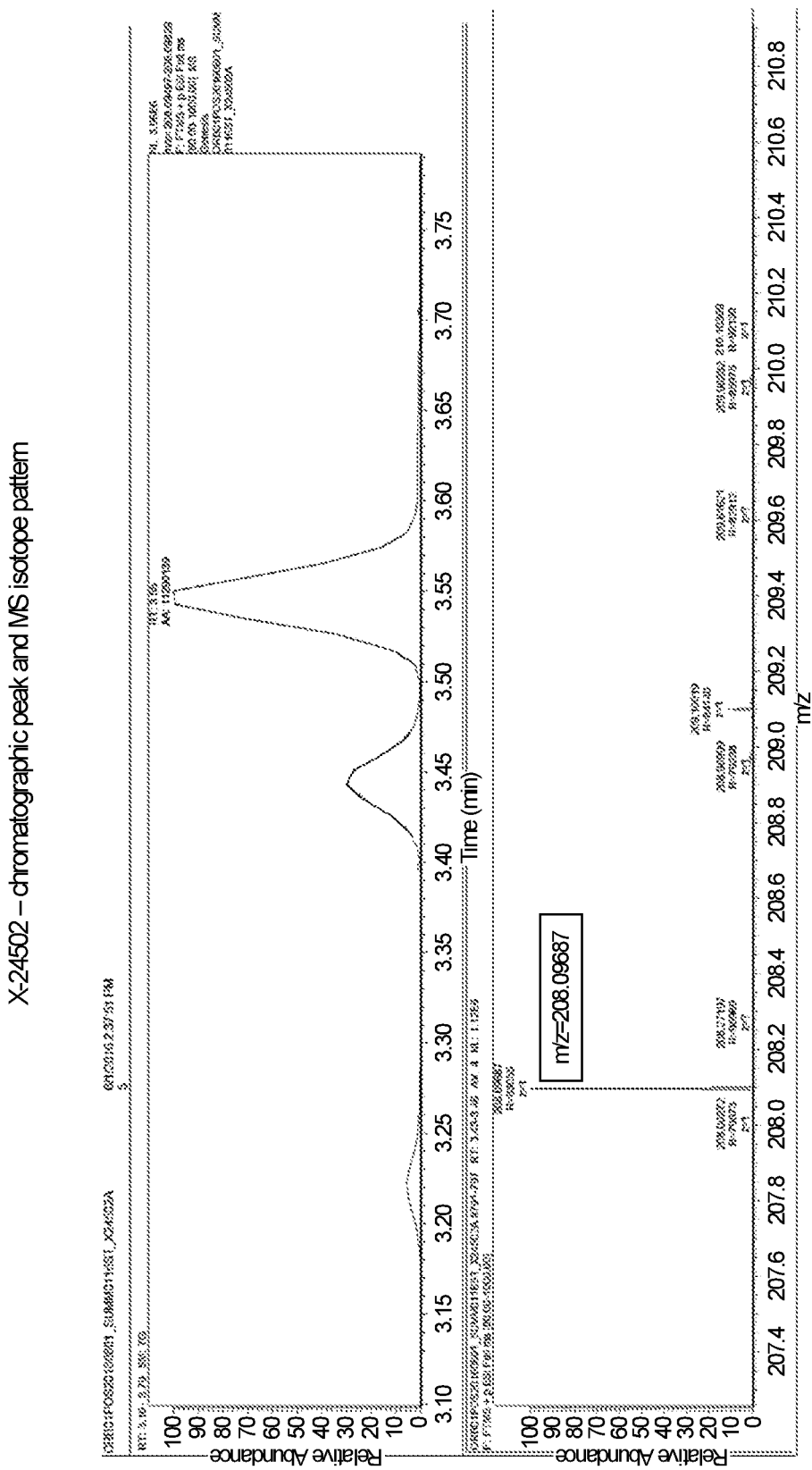
FIG. 23 shows LC/MS data for the metabolite X-24502.
Figures 1, 24:
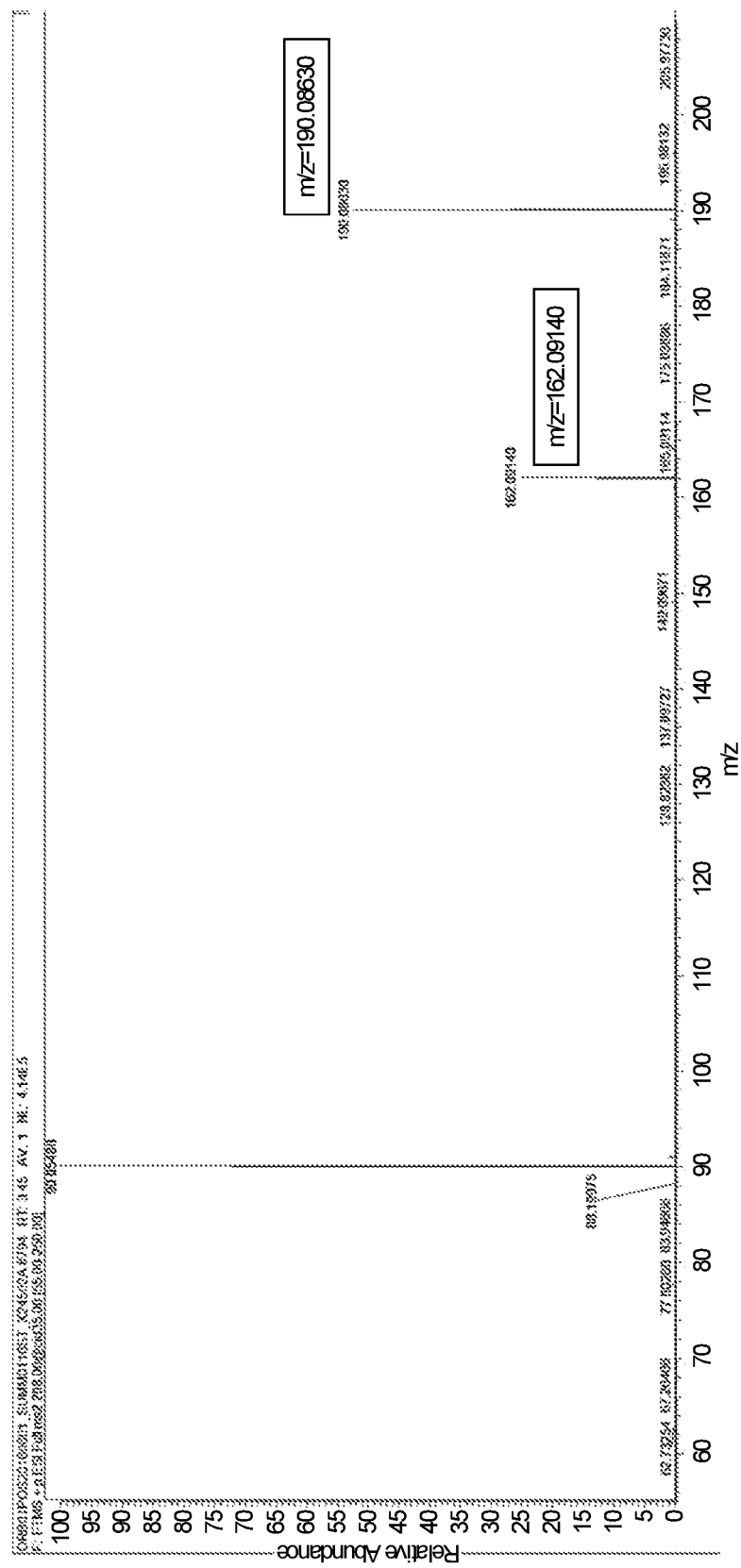
Figures 2, 24:
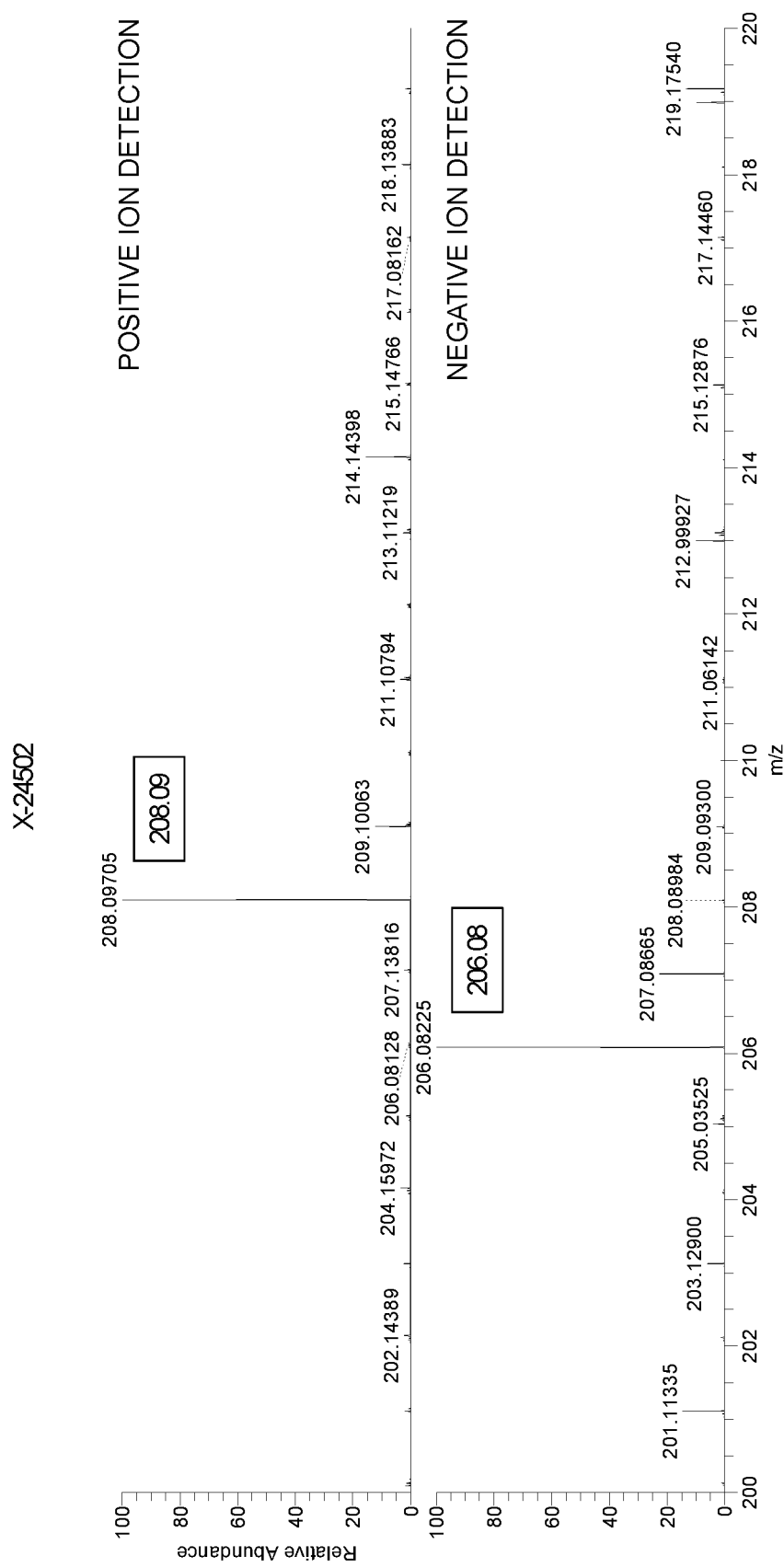
Figure 25:
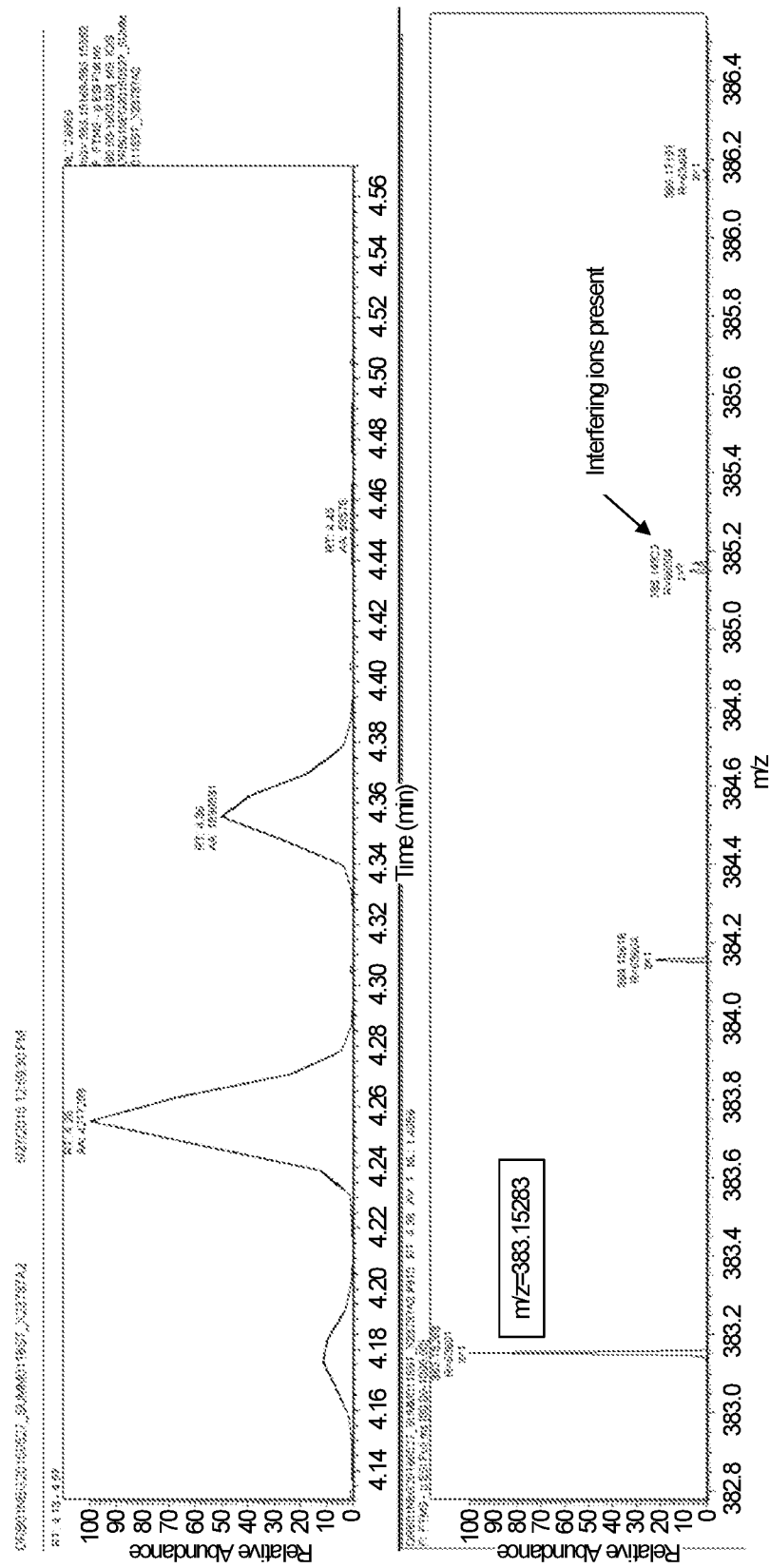
FIG. 25 shows LC/MS data for the metabolite X-23787.
Figures 1, 26:
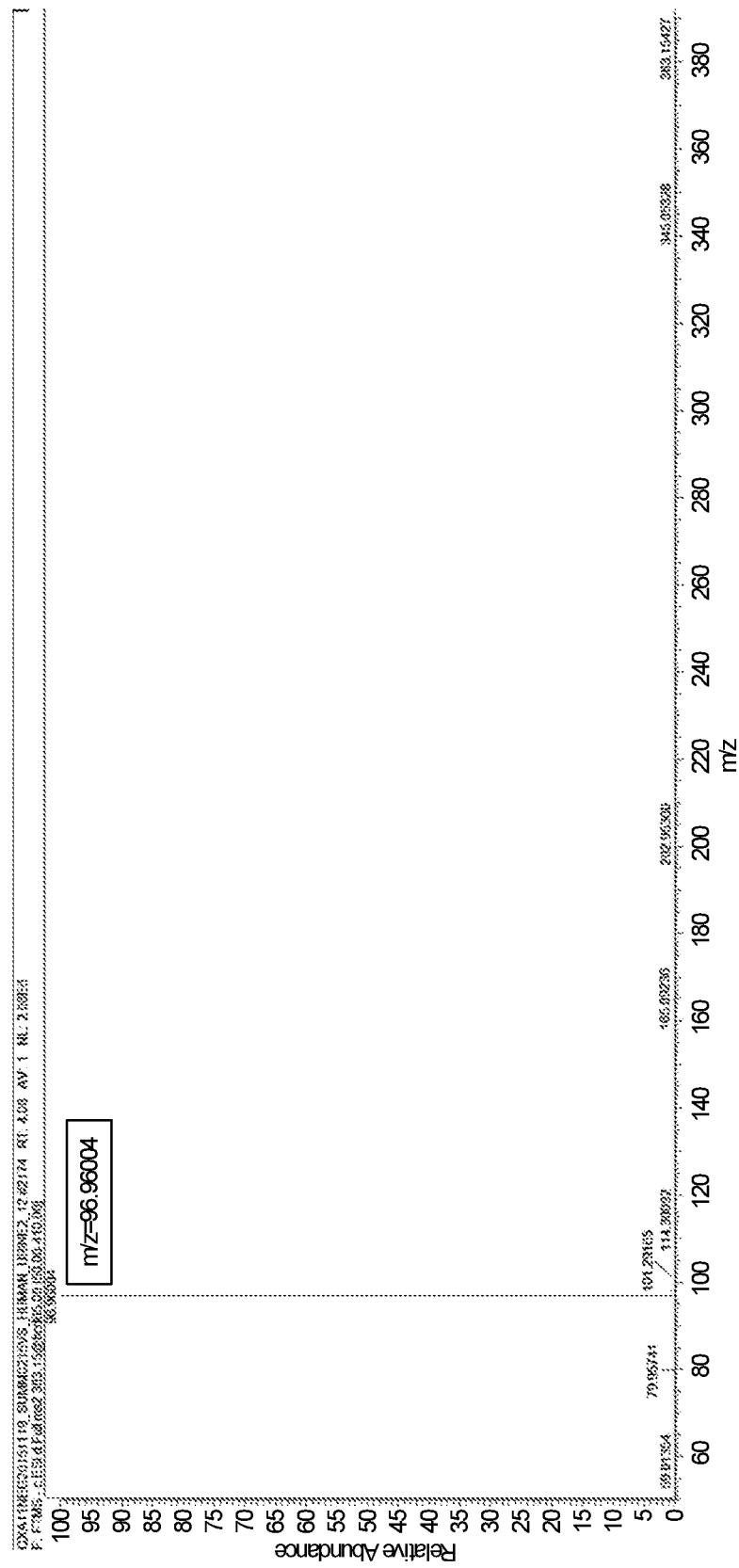
Figures 2, 26:
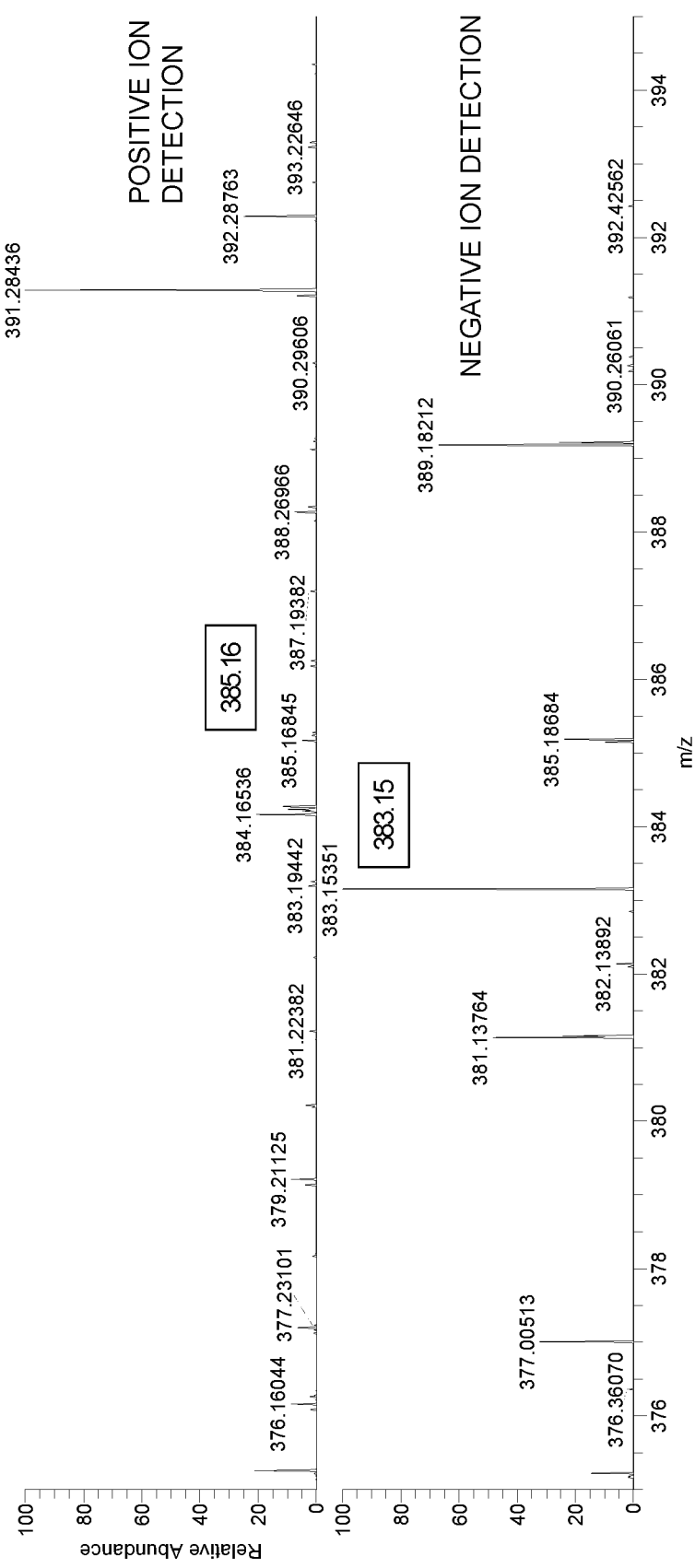

The LC/MS data for X-18126, X-24546, X-16567, X-11440, X-12831, X-12636, X-24502, and X-23787 are shown in FIGS. 10, 13, 15, 17, 19, 21, 23, and 25, respectively. In each drawing, the upper part shows a chromatograph by a liquid chromatography, and the lower part shows a mass spectrum obtained by a mass spectrometer. Further, the MS/MS data thereof are shown in FIGS. 11, 14, 16-1, 18, 20-1, 22-1, 24-1, and 26-1, respectively, and the MS/MS/MS data for X-18126 are shown in FIG. 12. The data in the positive ion detection mode and the negative ion detection mode of LC/MS of X-16567, X-12831, X-12636, X-24502, and X-23787 are shown in FIGS. 16-2, 20-2, 22-2, 24-2, and 26-2, respectively.

As a result of this analysis, it was confirmed that the mass of each metabolite is as follows:

X-18126 has a mass of 134.11 in the positive ion detection mode of LC/MS;

X-16567 has a mass of 188.12 in the positive ion detection mode of LC/MS and a mass of 186.11 in the negative ion detection mode of LC/MS;

X-24546 has a mass of 231.05 (divalent ion) in the negative ion detection mode of LC/MS;

X-11440 has a mass of 246.07 (divalent ion) in the negative ion detection mode of LC/MS;

X-12831 has a mass of 435.22 in the positive ion detection mode of LC/MS and a mass of 433.20 in the negative ion detection mode of LC/MS;

X-12636 has a mass of 259.16 in the positive ion detection mode of LC/MS and a mass of 257.15 in the negative ion detection mode of LC/MS;

X-24502 has a mass of 208.09 in the positive ion detection mode of LC/MS and a mass of 206.08 in the negative ion detection mode of LC/MS; and X-23787 has a mass of 385.16 in the positive ion detection mode of LC/MS and a mass of 383.15 in the negative ion detection mode of LC/MS.

As a result of the data analysis, X-18126 was found to be a compound having the following structure.

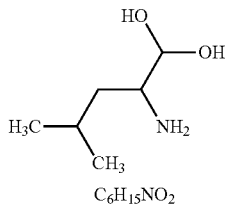

$C_6H_{15}NO_2$

Further, as a result of the data analysis, X-16567 was found to be a compound having the following structure.

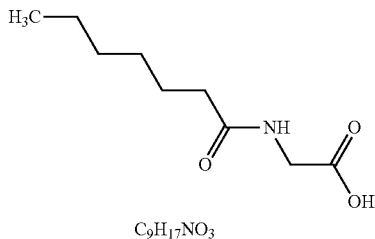

$C_9H_{17}NO_3$

All publications, patents, and patent applications cited herein are incorporated herein by reference in their entirety.

The invention claimed is:

1. A method for evaluating a cancer, comprising:
   measuring a urinary metabolite in a urine sample derived from a subject; and
   evaluating a breast cancer or a colon cancer in the subject based on the measurement results,
   wherein the urinary metabolite comprises a metabolite having a structure of $C_6H_{15}NO_2$ and which is measured to have a mass of 134.11 in the positive ion detection mode of liquid chromatography-mass spectrometry (LC/MS).

2. The method according to claim 1, wherein the urinary metabolite further comprises at least one urinary metabolite selected from the group consisting of the following urinary markers:
   a metabolite which is measured to have a mass of 188.12 in the positive ion detection mode of LC/MS and a mass of 186.11 in the negative ion detection mode of LC/MS;
   a metabolite which is measured to have a mass of 231.05 in the negative ion detection mode of LC/MS;
   a metabolite which is measured to have a mass of 246.07 in the negative ion detection mode of LC/MS;
   a metabolite which is measured to have a mass of 435.22 in the positive ion detection mode of LC/MS and a mass of 433.20 in the negative ion detection mode of LC/MS;
   a metabolite which is measured to have a mass of 259.16 in the positive ion detection mode of LC/MS and a mass of 257.15 in the negative ion detection mode of LC/MS;
   a metabolite which is measured to have a mass of 208.09 in the positive ion detection mode of LC/MS and a mass of 206.08 in the negative ion detection mode of LC/MS; and
   a metabolite which is measured to have a mass of 385.16 in the positive ion detection mode of LC/MS and a mass of 383.15 in the negative ion detection mode of LC/MS.

3. The method according to claim 1, wherein the evaluation of a breast cancer or a colon cancer is detection of a cancer in the subject, prediction of a cancer risk in the subject, determination of a cancer stage in the subject, determination of a cancer prognosis in the subject, or evaluation of the effect of a treatment on a cancer present in the subject.

4. The method according to claim 1, wherein the evaluation step comprises comparison with a reference selected from a measured value of the urinary metabolite in a sample of a healthy individual or a low risk individual, a measured value of the urinary metabolite in a sample of a patient having a cancer or a patient having a cancer at a known stage, a measured value of the urinary metabolite in a sample of a patient having a cancer with a specific prognosis, and a measured value of the urinary metabolite in a sample of the subject obtained at different time point.

5. The method according to claim 4, wherein when the reference is derived from a healthy individual or an individual with a low cancer risk, a case where the measured value of the metabolite which is measured to have a mass of 134.11 in the positive ion detection mode is lower than the reference indicates that a cancer is present in the subject, a cancer has developed, or a cancer has progressed.

6. The method according to claim 4, wherein when the reference is derived from a patient having a specific cancer or a patient having a cancer at a known stage or a patient having a cancer with a specific prognosis, a case where the measured value of the metabolite which is measured to have a mass of 134.11 in the positive ion detection mode is equivalent to the reference or shows no significant difference from the reference or is lower than the reference indicates that the subject has the cancer or has developed the specific cancer or has developed the cancer at the known stage or has the specific prognosis.

7. The method according to claim 1, wherein the measurement of the urinary metabolite is performed by liquid chromatography-mass spectrometry (LC/MS).

* * * * *